United States Patent
Ignatova et al.

(10) Patent No.: US 12,077,754 B2
(45) Date of Patent: *Sep. 3, 2024

(54) SYNTHETIC TRANSFER RNA WITH EXTENDED ANTICODON LOOP

(71) Applicant: ARCTURUS THERAPEUTICS, INC., San Diego, CA (US)

(72) Inventors: Zoya Ignatova, Hamburg (DE); Andrew Torda, Hamburg (DE); Marco Matthies, Hamburg (DE)

(73) Assignee: Arcturus Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/876,803

(22) Filed: Jul. 29, 2022

(65) Prior Publication Data
US 2023/0183685 A1 Jun. 15, 2023

Related U.S. Application Data

(63) Continuation of application No. 16/980,927, filed as application No. PCT/EP2019/056429 on Mar. 14, 2019, now Pat. No. 11,434,485.

(30) Foreign Application Priority Data

Mar. 15, 2018 (DE) .................. 10 2018 106 080.7
Mar. 15, 2018 (LU) ................... LU100734

(51) Int. Cl.
*C12N 15/11* (2006.01)
*A61K 48/00* (2006.01)

(52) U.S. Cl.
CPC .............. *C12N 15/11* (2013.01); *A61K 48/00* (2013.01); *C12N 2310/3513* (2013.01); *C12N 2310/531* (2013.01)

(58) Field of Classification Search
CPC ...................................................... C12N 15/11
See application file for complete search history.

(56) References Cited

U.S. PATENT DOCUMENTS

| 6,964,859 B2 | 11/2005 | Rajbhandary et al. |
| 11,434,485 B2 | 9/2022 | Ignatova et al. |
| 2020/0407714 A1 | 12/2020 | Ignatova et al. |

FOREIGN PATENT DOCUMENTS

WO WO-2007124493 A2 * 11/2007 ............. C12N 15/11

OTHER PUBLICATIONS

Anderson et al., Exploring the Limits of Codon and Anticodon Size, Chemistry and Biology, 2002, vol. 9: 237-244 (Year: 2002).*
Bozon et al., Identification of Four New Mutations in the Cystic Fibrosis Transmembrane Conductance Regulator Gene: IMT, L1077P, Y1092X, 2183Allk+G, Human Mutation, 1994, 3: 330-332 (Year: 1994).*
GenBank NM_000492.4, CFTR mRNA and protein sequence, 1992, pp. 1-11 (Year: 1992).*
Breitschopf et al., Identity elements of human tRNALeu: structural requirements for converting human tRNASer into a leucine acceptor in vitro, Nucleic Acids Research, 1995, vol. 23, No. 18, pp. 3633-3637 (Year: 1995).*
Maini et al, Ribosome-Mediated Incorporation of Dipeptides and Dipeptide Analogues into Proteins in Vitro, JACS, 2015, 137: 11206-11209 (Year: 2015).*
Ohashi et al., Primary Sequence of Glutamic Acid tRNA II From *Escherichia coli*, FEBS Letters, 1972, vol. 20, 2: 239-241 (Year: 1972).*
Atkinson et al. (Apr. 25, 1994) "Mutations to Nonsense Codons in Human Genetic Disease: Implications for Gene Therapy by Nonsense Suppressor TRNAs", Nucleic Acids Research, 22(8):1327-1334.
Auffinger et al. (2001) "An Extended Structural Signature for the tRNA Anticodon Loop", Cambridge University Press, Printed in the USA, 7:344-341.
Burnett et al. (2008) "RNA-based Therapeutics—Current Progress and Future Prospects", Chemistry and biology, 19(1):60-71.
Gambari et al., (Aug. 24, 2015) "Therapy for Cystic Fibrosis Caused by Nonsense Mutations", 13:309-326.
Geslain et al. (Feb. 2010) "Functional Analysis of Human tRNA Isodecoders", Journal of Molecular Biology, 396(3):821.
Koukuntla et al. (2009) "Suppressor tRNA Mediated Gene Therapy", Iowa State University, Graduate Theses and Dissertations, 1-116.
Lueck et al. (Nov. 20, 2016) "Engineered tRNA Suppression of a CFTR Nonsense Mutation", bioRxiv preprint first posted online, 1-9.

* cited by examiner

*Primary Examiner* — Ekaterina Poliakova-Georgantas
(74) *Attorney, Agent, or Firm* — Mintz, Levin, Cohn, Ferris, Glovsky, Popeo, P.C.

(57) ABSTRACT

The invention relates to a synthetic transfer RNA with an extended anticodon loop. The invention provides a synthetic suppressor transfer RNA useful for the treatment of a genetic disease like cystic fibrosis associated with a nonsense mutation. The synthetic transfer RNA contains an extended anticodon loop with two consecutive anticodon base triplets configured to base-pair to two consecutive codon base triplets on an mRNA. The first anticodon base triplet or the second anticodon base triplet is configured to base-pair to a stop codon base triplet on the mRNA.

19 Claims, 8 Drawing Sheets

Figure 1:
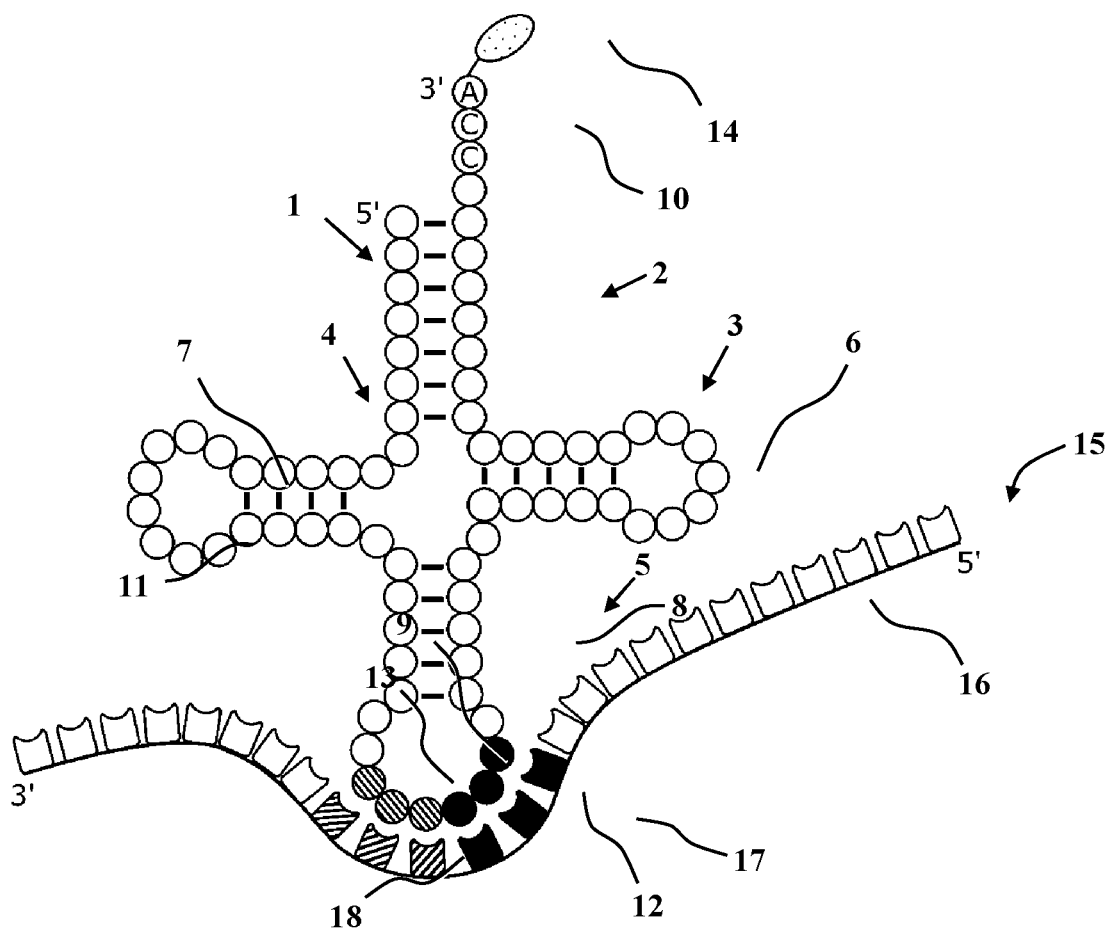

Specification includes a Sequence Listing.

SYNTHETIC TRANSFER RNA WITH EXTENDED ANTICODON LOOP

CROSS REFERENCE TO RELATED APPLICATIONS

This application is a continuation of U.S. patent application Ser. No. 16/980,927, filed Sep. 15, 2020, which is a U.S. National Phase of International Application PCT/EP2019/056429, filed Mar. 14, 2019, which claims the benefit of priority to German Application No. 10 2018 106 080.7 and Luxembourg Application No. LU100734, both of which were filed Mar. 15, 2018, each of which is incorporated by reference in their entirety for all purposes.

SEQUENCE LISTING

A Sequence Listing is provided herewith as a text file, "049386-536C01US_SL_ST26_REPLACEMENT_2.xml" created on Feb. 14, 2023 and having a size of 113,914 bytes. The contents of the text file are incorporated by reference herein in their entirety.

The invention relates to a synthetic transfer RNA with an extended anticodon loop.'

Transfer ribonucleic acids (tRNAs) are an essential part of the protein synthesizing machinery of living cells and are necessary components for translating the nucleotide sequence of a messenger RNA (mRNA) into the amino acid sequence of a protein. Naturally occurring tRNAs comprise an amino acid-binding stem being able to covalently bind an amino acid and an anticodon loop containing a base triplet called "anticodon", which can bind non-covalently to a corresponding base triplet called "codon" on an mRNA. A protein is synthesized by assembling the amino acids carried by tRNAs using the codon sequence on the mRNA as a template with the aid of a multi component system comprising, i.a., the ribosome and several auxiliary enzymes.

Some diseases belonging to the group of genetic disorders are based on a change in genetic information, e.g. a mutation in the DNA of the encoding genes. In this case the mRNA transcribed from the mutated gene will also carry the altered genetic information and an aberrant, possibly non-functional protein is formed. A mutation may, for example, lead to the introduction of a stop codon within a coding region, resulting in premature termination of protein synthesis and the production of a truncated protein. As an example, disease cystic fibrosis (CF) can be caused by a mutation of the gene coding for the membrane protein "cystic fibrosis transmembrane conductance regulator" (CFTR). In this case, the mutation introduces a premature termination codon (PTC) or stop codon within the reading frame of the CFTR gene (Vallières E, Elborn J S, Cystic fibrosis gene mutations: evaluation and assessment of disease severity. Advances in Genomics and Genetics, Volume 2014:4 Pages 161-172; Wilschanski M. Class 1 CF Mutations. Frontiers in Pharmacology. 2012; 3:117. doi: 10.3389/fphar.2012.00117; Gambari R, Breveglieri G, Salvatori F, Finotti A, Borgatti M, 2015, Therapy for Cystic Fibrosis Caused by Nonsense Mutations, Cystic Fibrosis in the Light of New Research, Wat D. (Ed.), InTech, DOI: 10.5772/61053).

Stop codon suppressor agents like aminoglycosides promoting translational readthrough for recovering a functional CFTR in CF with PTCs have been described in the scientific literature (see, e.g., Mutyam V, Du M, Xue X, Keeling K M, White E L, Bostwick J R, Rasmussen L, Liu B, Mazur M, Hong J S, Falk Libby E, Liang F, Shang H, Mense M, Suto M J, Bedwell D M, Rowe S M. Discovery of Clinically Approved Agents That Promote Suppression of Cystic Fibrosis Transmembrane Conductance Regulator Nonsense Mutations. Am J Respir Crit Care Med. 2016 Nov. 1; 194(9):1092-1103. doi 10.1164/rccm.201601-01540C; Gambari R, Breveglieri G, Salvatori F, Finotti A, Borgatti M, 2015, Therapy for Cystic Fibrosis Caused by Nonsense Mutations, Cystic Fibrosis in the Light of New Research, Wat D. (Ed.), InTech, DOI: 10.5772/61053). Such agents, however, are often neither effective nor well tolerated.

Although still in its beginnings, gene therapy involving the introduction of corrective genetic material into the cells of a patient, is becoming more and more important for treating genetic diseases. Currently, gene therapy approaches are primarily based on the use of mRNA in order to replace and compensate for a mutated "defective" mRNA. However, mRNA is short-lived and the length of the mRNA sequences presents problems for therapeutic application. A particular mRNA may, for example, be longer than the cargo capacity of currently available vectors for gene delivery and therapy.

Compared to mRNA, tRNA molecules offer significantly higher stability and are on average 10-fold shorter, alleviating the problem of introduction into the target tissue. This has led to attempts to use tRNA in gene therapy in order to prevent the formation of a truncated protein from an mRNA with a premature stop codon and to introduce the correct amino acid instead (see, e.g., Koukuntla, R 2009, Suppressor tRNA mediated gene therapy, Graduate Theses and Dissertations, 10920, Iowa State University, http://lib.dr.iastate.edu/etd/10920; US 2003/0224479 A1; U.S. Pat. No. 6,964,859).

Lueck et al. (Lueck, J. D., Infield, D T, Mackey, A L, Pope, R M, McCray, P B, Ahern, C A. Engineered tRNA suppression of a CFTR nonsense mutation, bioRxiv 088690; doi: 10.1101/088690), for example, describe a codon-edited tRNA enabling the conversion of an in-frame stop codon in the CFTR gene to the naturally occurring amino acid in order to restore the full-length wild type protein.

Sako et al. (Sako Y, Usuki F, Suga H. A novel therapeutic approach for genetic diseases by introduction of suppressor tRNA. Nucleic Acids Symp Ser (Oxf). 2006; (50):239-40. PubMed PMID: 17150906, doi: 10.1093/nass/nrl119) describe an approach to read through PTC-containing mRNAs using suppressor tRNA that is introduced to cells by transfection. Nonsense triplet codons were suppressed and four-base codons were read by the corresponding suppressor tRNAs derived from human tRNA(Ser).

tRNAs with an extended anticodon loop comprising a four-base or five-base anticodon have also been described for incorporating unnatural amino acids into proteins (US 2006/0177900 A1; WO 2005/007870; Hohsaka T, Ashizuka Y, Murakami H, Sisido M. Five-base codons for incorporation of nonnatural amino acids into proteins. Nucleic Acids Research. 2001; 29(17):3646-3651; Hohsaka T, Sisido M. Incorporation of non-natural amino acids into proteins. Curr Opin Chem Biol. 2002 December; 6(6):809-15. Review. PubMed PMID: 12470735). Anderson et al. (Anderson J C, Magliery T J, Schultz P G. Exploring the limits of codon and anticodon size. Chem Biol. 2002 February; 9(2):237-44. DOI: 10.1016/S1074-5521(02)00094-7) describe the suppression of two-, three-, four-, five-, and six-base codons with tRNAs containing 6-10 nt in their anticodon loops.

There is still a need for counteracting the effects of and/or suppressing a nonsense mutation. It is therefore an object of the invention to provide such means, in a particular a nonsense mutation suppressor for the treatment of a genetic disease like cystic fibrosis associated with a nonsense mutation.

In one aspect the invention provides a synthetic transfer ribonucleic acid (tRNA), the synthetic transfer RNA comprising an extended anticodon loop with two consecutive anticodon base triplets configured to base-pair to two consecutive codon base triplets on an mRNA, wherein the first anticodon base triplet or the second anticodon base triplet is configured to base-pair to a stop codon base triplet on the mRNA.

The invention provides novel suppressor tRNAs that can be used to suppress a nonsense mutation, e.g. for restoring the ability of a cell to synthesize a functional protein from an mRNA having a mutation in its coding sequence, which would otherwise lead to premature cessation of translation and a truncated protein. The synthetic tRNA of the invention comprises an extended anticodon loop having two consecutive anticodon base triplets, at least one of which being able to base-pair to a stop codon base triplet on an mRNA. The synthetic tRNA of the invention is thus able to bind to two adjacent codons on the mRNA, one being a premature termination codon (PTC), which are complementary to the two anticodon base triplets. The synthetic tRNA of the invention not only base-pairs with the PTC but also with the preceding or following codon on the mRNA resulting in the incorporation of an amino acid carried by the tRNA into the growing amino acid chain instead of a premature termination of the protein synthesis. Unless the synthetic tRNA of the invention is (pre)aminoacylated with a dipeptide, the resulting protein will have one amino acid less than the wild-type protein, i.e. a protein synthesized from the wild-type mRNA without the PTC, but the chances are good that this will nevertheless lead to a functional protein. Advantageously, the base-pairing of the synthetic tRNA of the invention with two adjacent codons, one of which being a PTC and the other being a specific codon adjacent to the PTC, on the mRNA is associated with higher specificity compared to suppressor tRNAs binding only to a single codon, i.e. a stop codon. Consequently, the synthetic tRNA of the invention can be designed to only bind to a specific combination of a PTC and one of its neighbouring codons, considerably reducing the risk of unwanted pairing to PTCs or "normal" stop codons on non-targeted mRNA.

The terms "transfer ribonucleic acid" or "tRNA" refer to RNA molecules with a length of typically 73 to 90 nucleotides, which mediate the translation of a nucleotide sequence in messenger RNA into the amino acid sequence of a protein. tRNAs are able to covalently bind a specific amino acid at their 3' CCA tail at the end of the acceptor stem, and to base-pair via a three-nucleotide anticodon in the anticodon loop of the anticodon arm with a three-nucleotide sequence (codon) in the messenger RNA. Some anticodons can pair with more than one codon due to a phenomenon known as wobble base pairing. The secondary "cloverleaf" structure of tRNA comprises the acceptor stem binding the amino acid and three arms ("D arm", "T arm" and "anticodon arm") ending in loops (D loop, $T_\psi C$ loop, anticodon loop), i.e. sections with unpaired nucleotides. Aminoacyl tRNA synthetases charge (aminoacylate) tRNAs with a specific amino acid. Each tRNA contains a distinct anticodon triplet sequence that can base-pair to one or more codons for an amino acid. By convention, the nucleotides of tRNAs are often numbered 1 to 76, starting from the 5'-P terminus, based on a "consensus" tRNA molecule consisting of 76 nucleotides, and regardless of the actual number of nucleotides in the tRNA, which may deviate from 76 due to variable portions, e.g. the D loop, in the tRNA (see FIG. 3). Following this convention (also "tRNA numbering convention" in the following), nucleotide positions 34-36 of naturally occurring tRNA refer to the three nucleotides of the anticodon, and positions 74-76 refer to the terminating CCA tail. Any "supernumerary" nucleotide can, e.g., be numbered by adding alphabetic characters to the number of the previous nucleotide being part of the consensus tRNA and numbered according to the convention, for example 20a, 20b etc, or by independently numbering the nucleotides and adding a leading letter, as in case of the variable loop such as e11, e12 etc. (see, for example, Sprinzl M, Horn C, Brown M, Ioudovitch A, Steinberg S. Compilation of tRNA sequences and sequences of tRNA genes. Nucleic Acids Res. 1998; 26(1): 148-53).

The terms "synthetic transfer ribonucleic acid" or "synthetic tRNA" refer to a non-naturally occurring tRNA. The term also encompasses analogues to naturally occurring tRNAs, i.e. tRNAs being structurally similar to naturally occurring tRNAs, but being modified in the base component, the sugar component and/or the phosphate component of one or more of the nucleotides, of which the tRNA is composed. The modified tRNA may, for example, have the phosphodiester backbone modified in that the phosphodiester bridge is replaced by a phosphorothioate, phosphoramidate or methyl phosphonate bridge. The sugar component may, for example, be modified at the 2' OH group, e.g. by dehydroxylating it to a deoxy ribonucleotide, or by replacing it with a methoxy-, methoxyethoxy- or aminoethoxy group. A synthetic transfer ribonucleic acid can, for example, be synthesized chemically and/or enzymatically in vitro, or in a cell based system, e.g. in a bacterial cell in vivo.

The term "codon" refers to a sequence of nucleotide triplets, i.e. three DNA or RNA nucleotides, corresponding to a specific amino acid or stop signal during protein synthesis. A list of codons (on mRNA level) and the encoded amino acids are given in the following:

| Amino acid | One Letter Code | Codons |
|---|---|---|
| Ala | A | GCU, GCC, GCA, GCG |
| Arg | R | CGU, CGC, CGA, CGG, AGA, AGG |
| Asn | N | AAU, AAC |
| Asp | D | GAU, GAC |
| Cys | C | UGU, UGC |
| Gln | Q | CAA, CAG |
| Glu | E | GAA, GAG |
| Gly | G | GGU, GGC, GGA, GGG |
| His | H | CAU, CAC |
| Ile | I | AUU, AUC, AUA |
| Leu | L | UUA, UUG, CUU, CUC, CUA, CUG |
| Lys | K | AAA, AAG |
| Met | M | AUG |
| Phe | F | UUU, UUC |
| Pro | P | CCU, CCC, CCA, CCG |

-continued

| Amino acid | One Letter Code | Codons |
|---|---|---|
| Ser | S | UCU, UCC, UCA, UCG, AGU, AGC |
| Thr | T | ACU, ACC, ACA, ACG |
| Trp | W | UGG |
| Tyr | Y | UAU, UAC |
| Val | V | GUU, GUC, GUA, GUG |

START: AUG
STOP: UAA, UGA, UAG, abbreviated "X"

The term "sense codon" as used herein refers to a codon coding for an amino acid. The term "stop codon" or "nonsense codon" refers to a codon, i.e. a nucleotide triplet, of the genetic code not coding for one of the 20 amino acids normally found in proteins and signalling the termination of translation of a messenger RNA. Stop codons (on the mRNA level) are UAA ("ochre"), UAG ("amber"), or UGA ("opal"). When describing the sequence of a protein, "X" (in one-letter code) or "Ter" (in three-letter code) is used to denote a stop codon. A nonsense mutation in a protein is often denoted with the wild-type amino acid, followed by the position of the amino acid in the protein, and an "X". As an example, "R553X" denotes a mutation of the codon coding for arginine (one-letter code R) to a stop codon (X) at position 553 in the protein (CFTR). A stop codon in an mRNA within an open reading frame leads to the production of a truncated, mostly non-active protein fragment.

The term "anticodon" refers to a sequence of three nucleotides that are complementary, that is bind or base-pair, to the three bases of the codon on the mRNA. If used herein, the terms "corresponding anticodon" or "corresponding codon" relate to an anticodon or a codon, which base-pairs with the respective complementary codon or anticodon. An anticodon may also contain nucleotides with modified bases.

The term "anticodon loop" refers to the unpaired nucleotides of the anticodon arm containing the anticodon. In naturally occurring tRNAs the anticodon loop is usually comprised of seven nucleotides, three of which pair to the codon in the mRNA.

The term "extended anticodon loop" refers to an anticodon loop with a higher number of nucleotides in the loop than in naturally occurring tRNAs. An extended anticodon loop may, for example, contain more than seven nucleotides, e.g. eight, nine, ten or eleven nucleotides.

The terms "codon base triplet" or "anticodon base triplet" refer to sequences of three consecutive nucleotides representing a codon or anticodon. The terms are used in order to clarify that the terms "codon" or "anticodon" as used herein in relation to the invention refer to nucleotide triplets, and not to sequences of four or more nucleotides, e.g. nucleotide quadruplets ("four base codons") etc. The two consecutive anticodon base triplets in the anticodon loop of a synthetic tRNA of the invention may, however, also be called "anticodon pair", "anticodon double", "anticodon duplex", "2×3nt anticodon" or "anticodon tandem", and, correspondingly, the two consecutive codon base triplets in the mRNA "codon pair", "codon double", "codon duplex", "2×3nt codon" or "codon tandem".

The term "base pair" refers to a pair of bases joined by hydrogen bonds. One of the bases of the base pair is usually a purine, and the other base is usually a pyrimidine. In RNA the bases adenine and uracil can form a base pair and the bases guanine and cytosine can form a base pair. However, the formation of other base pairs ("wobble base pairs") is also possible, e.g. base pairs of guanine-uracil (G-U), hypoxanthine-uracil (I-U), hypoxanthine-adenine (I-A), and hypoxanthine-cytosine (I-C). The term "being able to base-pair" refers to the ability of nucleotides or sequences of nucleotides to form hydrogen-bond-stabilized structures with a complementary nucleotide or nucleotide sequence.

The term "PTC" refers to a premature termination codon, i.e. a stop codon introduced into a coding nucleic acid sequence by a nonsense mutation, i.e. a mutation in which a sense codon, coding for one of the twenty proteinogenic amino acids specified by the standard genetic code, is changed to a chain-terminating codon. The term thus refers to a premature stop signal in the translation of the genetic code contained in mRNA. PTCs are implicated in a variety of genetic disorders, e.g. cystic fibrosis (DF), Duchenne muscular dystrophy (DMD), neurofibromatosis type 1 (NF1) or Hurler syndrome (MPS I). The term "premature stop codon" ("PSC") may be used synonymously for a premature termination codon, PTC.

The term "cystic fibrosis" refers to a genetic disorder inherited in an autosomal recessive manner. It is caused by mutations in both copies of the gene for the cystic fibrosis transmembrane conductance regulator (CFTR) protein. The term "nonsense mutation cystic fibrosis" (nmCF) may be used for CF caused by a nonsense mutation. Examples for nonsense mutation in the CFTR are W1282X (X=stop codon), G542X, R553X or R1162X.

The term "Duchenne muscular dystrophy" (DMD) (also "Becker muscular dystrophy", BMD) refers to a X-linked recessive genetic disorder characterized by progressive muscle degeneration and weakness caused by an absence of a functional dystrophin protein. The absence of dystrophin can be caused by a nonsense mutation in the dystrophin gene.

The term "neurofibromatosis type 1" (NF1 or NF-1), also called "Recklinghausen disease", is an autosomal dominant inherited disorder caused by the mutation of the NF1 gene on chromosome 17 coding for neurofibromin. NF1 causes tumours along the nervous system.

The term "Hurler syndrome" (also mucopolysaccharidosis type I, MPS I), relates to a genetic disorder causing accumulation of mucopolysaccharides (glycosaminoglycans, GAGs) due to a deficiency in alpha-L iduronidase. The most common PTC mutations in Hurler syndrome are W402X and Q70X (Scott H S, Litjens T, Hopwood J J, Morris C P, 1992, A common mutation for mucopolysaccharidosis type I associated with a severe Hurler syndrome phenotype, Hum Mutat.1: 103-108, doi 10.1002/humu. 1380010204; Keeling K M, Brooks D A, Hopwood J J, Li P, Thompson J N, Bedwell D M, 2001, Gentamicin-mediated suppression of Hurler syndrome stop mutations restores a low level of α-1-iduronidase activity and reduces lysosomal glycosaminoglycan accumulation, Human Molecular Genetics 10, 291-300, doi 10.1093/hmg/10.3.291).

The terms "nonsense suppression" or "nonsense mutation suppression" refer to mechanisms masking the effects of a nonsense mutation and at least partly restoring the wild-type phenotype.

The term "suppressor tRNA" relates to a tRNA altering the reading of a messenger RNA in a given translation system. An example for a suppressor tRNA is a tRNA carrying an amino acid and being able to base-pair to a stop codon, so that the translation system can read through the stop codon. tRNAs that can recognize a stop codon are known as nonsense suppressor tRNAs or NSTs.

The term "homology" in relation to a nucleic acid refers to the degree of similarity or identity between the nucleotide sequence of the nucleic acid and the nucleotide sequence of another nucleic acid. Homology is determined by comparing a position in the first sequence with a corresponding position in the second sequence in order to determine whether identical nucleotides are present at that position. It may be necessary to take sequence gaps into account in order to produce the best possible alignment. For determining the degree of similarity or identity between two nucleic acids it is preferable to take a minimum length of the nucleic acids to be compared into account, for example at least 25%, 30%, 40%, 50%, 60%, 70%, 80%, 90%, 91%, 92%, 93%, 94%, 95%, 96%, 97%, 98%, 99%, 99.2% or 99.5% of the nucleotides in the respective sequences. Preferably the full length of the respective nucleic acid(s) is used for comparison. The degree of similarity or identity of two sequences can be determined by using a computer program such as muscle (Edgar, R. C. (2004), Muscle: multiple sequence alignment with high accuracy and high throughput, Nucleic Acids Research, 32, 1792-1797, doi: 10.1093/nar/gkh340) or mafft (Katoh, K. and Standley, D. M. (2013) MAFFT Multiple Sequence Alignment Software Version 7, Molecular Biology and Evolution, 30, 772-780, doi.org/10.1093/molbev/mst010). Where such terms like "x % homologous to" or "homology of x %" are used it means that two nucleic acid sequences have a sequence identity or similarity of x %, e.g. 50%.

The term "aminoacylation" relates to the enzymatic reaction charging a tRNA with an amino acid. An aminoacyl tRNA synthetase (aaRS) catalyses the esterification of a specific cognate amino acid or its precursor to a compatible cognate tRNA to form an aminoacyl-tRNA. The term "aminoacyl-tRNA" thus relates to a tRNA with an amino acid attached to it. Each aminoacyl-tRNA synthetase is highly specific for a given amino acid, and, although more than one tRNA may be present for the same amino acid, there is only one aminoacyl tRNA synthetase for each of the 20 proteinogenic amino acids. The terms "charge" or "load" may also be used synonymously for "aminoacylate". The term "aminoacylated" in relation to the synthetic tRNA of the invention relates to a synthetic tRNA already charged (precharged) with an amino acid or a dipeptide, such that the tRNA is already acylated when entering the target cell. The term "preaminoacylated" may synonymously be used in this context.

The term "modified nucleotides" (or "unusual nucleotides") in reference to tRNA relates to nucleotides having modified or unusual nucleotide bases, i.e. other than the usual bases adenine (A), uracil (U), guanine (G) and cytosine (C). Examples of modified nucleotides include 4-acetylcytidine (ac4c), 5-(carboxyhydroxymethyl)uridine (chm5u), 2'-O-methylcytidine (cm), 5-carboxymethylaminomethyl-2-thiouridine (cmnm5s2u), 5-carboxymethylaminomethyluridine (cmnm5u), dihydrouridine (d), 2'-O-methylpseudouridine (fm), beta, D-galactosylqueuosine (gal q), 2'-O-methylguanosine (gm), inosine (i), N6-isopentenyladenosine (i6a), 1-methyladenosine (m1a), 1-methylpseudouridine (m1f), 1-methylguanosine (m1g), 1-methylinosine (m1i), 2,2-dimethylguanosine (m22g), 2'-O-methyladenosine (am), 2-methyladenosine (m2a), 2-methylguanosine (m2g), 3-methylcytidine (m3c), 5-methylcytidine (m5c), N6-methyladenosine (m6a), 7-methylguanosine (m7g), 5-methylaminomethyluridine (mam5u), 5-methoxyaminomethyl-2-thiouridine (mam5s2u), beta, D-mannosylqueuosine (man q), 5-methoxycarbonylmethyl-2-thiouridine (mcm5s2u), 5-methoxycarbonylmethyluridine (mcm5u), 5-carbamoylmethyluridine (ncm5U), 5-carbamoylmethyl-2'-O-methyluridine (ncm5Um), 5-methoxyuridine (mo5u), 2-methylthio-N6-isopentenyladenosine (ms2i6a), N-((9-beta-D-ribofuranosyl-2-methylthiopurine-6-yl)carbamoyl) threonine (ms2t6a), N-((9-beta-D-ribofuranosylpurine-6-yl) N-methylcarbamoyl)threonine (mt6a), uridine-5-oxyacetic acid-methylester (mv), uridine-5-oxyacetic acid (05u), wybutoxosine (osyw), pseudouridine (p, Ψ), queuosine (q), 2-thiocytidine (s2c), 5-methyl-2-thiouridine (s2t), 2-thiouridine (s2u), 4-thiouridine (s4u), 5-methyluridine (t), N-((9-beta-D-ribofuranosylpurine-6-yl)-carbamoyl)threonine (t6a), 2'-O-methyl-5-methyluridine (tm), 2'-O-methyluridine (um), wybutosine (yw), 3-(3-amino-3-carboxy-propyl) uridine, (acp3)u (x).

The term "corresponding modified nucleotide" relates to a modified nucleotide at a given position in a sequence, which base has been modified based on the usual, i.e. unmodified, base of the nucleotide at the same position in the original sequence to be compared with the sequence containing the modified nucleotide. A corresponding modified nucleotide is thus any nucleotide that, in a cell, is usually produced from a usual nucleotide by modifying the usual nucleotide. A modified nucleotide corresponding to uridine, for example, is thus any nucleotide derived by the modification of uridine. As an example, 5-(carboxyhydroxymethyl)uridine (chm5u) at a particular position in a sequence may be a modified nucleotide corresponding to uridine at the same position in the original sequence. Further modified nucleotides corresponding to uridine are, for example, 5-methyluridine (t), 2'-O-methyl-5-methyluridine (tm), 2'-O-methyluridine (um), or 5-methoxyuridine (mo5u). Inosine, as another example, is produced from adenosine and thus is a modified nucleotide corresponding to adenosine.

The synthetic transfer RNA of the invention may be synthesized based on a naturally occurring tRNA. However, the tRNA of the invention is preferably designed computationally ("in silico") and synthesized chemically and/or enzymatically. The computational design of a synthetic tRNA according to the invention allows the design and synthesis of a tRNA that does not interfere with other tRNAs present in the cell. The synthetic tRNA of the invention is selected or designed in such a manner that an aminoacyl tRNA synthetase that naturally occurs in a living cell, preferably a mammalian cell, e.g. a human cell, is able to charge the tRNA with a specific amino acid. Preferably, the tRNA is selected or designed in such a manner that, under conditions within the cell, an amino acid is enzymatically attached to the tRNA that is encoded by the codon in a targeted mRNA next to a premature stop codon or by the wild-type codon mutated to the premature stop codon.

The skilled person is aware of the fact that a tRNA is aminoacylated with a specific amino acid by a specific aminoacyl tRNA synthetase (aaRS), and that the aaRS is able to recognize its cognate tRNA through unique identity elements at the acceptor stem and/or anticodon loop of the tRNA. In order to provide a tRNA which is loaded with its cognate amino acid in vivo, the skilled person will design the synthetic tRNA of the invention with suitable unique identity elements.

The tRNA of the invention preferably has a low sequence identity to any naturally occurring tRNA, and has preferably a sequence identity of less than 50%, especially preferred of less than 49%, 48%, 47%, 46%, 45%, 44% or 43%.

In the synthetic transfer RNA according to the invention the anticodon loop has been extended by a large enough number of nucleotides to accommodate the anticodon pair and to allow base-pairing with an mRNA. The anticodon loop of a synthetic transfer RNA of the invention may, for example, consist of 8-12, preferably 9-11, further preferred 9 or 10 nucleotides. An anticodon loop of 9 nucleotides is especially preferred.

The extended anticodon loop of the synthetic tRNA of the invention comprises two consecutive anticodon base triplets, which are configured to base-pair to two consecutive codon base triplets on an mRNA, the latter preferably being a targeted mRNA carrying a premature termination codon (PTC). One of the anticodon base triplets is configured to base-pair to a stop codon base triplet on the mRNA, whereas the neighbouring anticodon base triplet preferably is configured to base-pair to a sense codon preceding or following, i.e. 5' or 3' to the stop codon base triplet on the mRNA. The terms "preceding" or "following" relate to the direction of translation, i.e. the 5'-3' direction of the mRNA.

An example of an anticodon pair in the extended anticodon loop of the synthetic tRNA of the invention is UGCUCA (in 5'-3' direction, or ACUCGU in 3'-5' direction), matching with UGAGCA (5'-3') in the mRNA, where UCA is able to base-pair with the stop codon UGA, and UGC is able to base-pair with the codon GCA coding for alanine.

It is preferred that the two consecutive anticodon base triplets are asymmetrically arranged in the extended anticodon loop of the transfer RNA. "Asymmetrically arranged" in this context means that the 6nt sequence composed of the two consecutive anticodon base triplets ("anticodon tandem") is, in a two-dimensional representation of the anticodon arm, arranged offset from an imaginary symmetry axis longitudinally traversing through the stem of the anticodon loop and extended in the direction of the anticodon loop (see also FIG. 2). For example, the anticodon tandem may be arranged within the anticodon loop such that four of the six nucleotides forming the anticodon tandem lie to one side of the axis, and the other two nucleotides lie on the other side of the axis. In other words, within the anticodon loop, the number of nucleotides flanking the anticodon tandem to the 3'-end and the 5'-end of the tRNA is not the same. There may be more nucleotides within the anticodon loop flanking the anticodon tandem to the 3'-end than to the 5'-end, or vice versa. It is to be noted in this context that, for an asymmetric arrangement of the anticodon tandem in the anticodon loop, it is only required that the larger share of the anticodon tandem is arranged offset the axis, without it being necessary that this always involves whole nucleotides. In a symmetric arrangement the anticodon tandem would be arranged in a manner that three nucleotides would be on one side and three on the opposite side of the axis.

In a preferred embodiment of the synthetic transfer RNA of the invention the two consecutive anticodon base triplets are offset to the 3'-end of the synthetic transfer RNA, i.e. there are more nucleotides within the anticodon loop flanking the anticodon tandem to the 5'-end.

In a preferred embodiment of the invention, the synthetic transfer RNA is further optimized, i.e. structurally modified, to enhance translation readthrough. The tRNA of the invention is thus preferably structurally, that is in terms of its nucleotide sequence, so designed that the tRNA body is adapted to the specific anticodon tandem and/or anticodon loop used in order to result in a maximum readthrough in vivo. The tRNA may, for example, be further modified regarding the nucleotide composition of its components outside the anticodon arm, for example of its T-arm, D-arm or variable loop. The term "translation readthrough" relates to the synthesis of a complete protein from an mRNA having a premature stop codon (PTC) within its sequence, i.e. to the translation of an mRNA with a PTC beyond the PTC, such that a complete and functional protein results, although the protein may lack an amino acid compared to the wild type protein. The expression "enhance translation readthrough" relates to the synthesis of a higher share of complete proteins from an mRNA comprising a PTC in the presence of a further modified tRNA compared to the translation involving a tRNA, which has not been further modified.

In a preferred embodiment, the T-stem is modified to be composed of a first five nucleotide T-stem sequence AGGGG and a second five nucleotide T-stem sequence CCCCU, wherein the second T-stem sequence is complementary to the first T-stem sequence and is arranged, in 5'-3' direction in relation to the tRNA, after the T-loop. The T-arm thus has the structure 5'-AGGGG-(T-Loop)-CCCCU-3'. With reference to a canonical tRNA (see FIG. 3) the sequence AGGGG would occupy the positions 49 to 53 according to the standard consensus numbering of tRNAs, and the corresponding nucleotide sequence CCCCU (in 5'-3' direction) positions 61 to 65.

Further, the tRNA of the invention may, additionally or alternatively, be modified in the sequence of its D arm. The tRNA of the invention may, for example, be modified to have a D arm having the sequence GCGCAGCCUG-GUAGCGC (SEQ ID NO: 31). In a preferred embodiment, the tRNA of the invention has the T-stem sequence described above and the D arm sequence of SEQ ID NO: 31.

The variable loop of the tRNA of the invention may also be modified in order to enhance translation readthrough. The variable loop may be modified alone or together with the T-stem and/or D arm. For example, the variable loop of the natural tRNA$^{Sec}$ (Selenocysteine tRNA), given in SEQ ID NO: 54, UUGGGGCCGCGCGGUCCCGG), or a modified variant thereof, may be incorporated. A modified variant of the tRNA$^{Sec}$ V-loop may have a shortened or extended sequence, or a sequence wherein one or more nucleotides are replaced with other nucleotides.

The synthetic transfer RNA according to the invention may be aminoacylated, i.e. carrying an amino acid or a dipeptide at the end of its acceptor stem. Preferably, the tRNA is aminoacylated with an amino acid being encoded by a sense codon base-pairing with one of the anticodon pairs or with an amino acid being encoded by a codon mutated to a premature termination codon and base-pairing with the other anticodon pair. The synthetic tRNA of the invention can be chemically and/or enzymatically aminoacylated with a single amino acid or dipeptide. The loading of a tRNA with a dipeptide can be accomplished with methods known to those skilled in the art (see, for example, Maini R, Dedkova L M, Paul R, Madathil M M, Chowdhury S R, Chen S, Hecht S M, 2015, Ribosome-Mediated Incorporation of Dipeptides and Dipeptide Analogues into Proteins in Vitro, J. Am. Chem. Soc., 137, 11206-11209, doi 10.1021/jacs.5b03135). Engineered bacterial tRNA synthetases or RNA-based catalysts may, for example, be used to aminoacylate the tRNA with a dipeptide. A dipeptide is preferably composed of the amino acids encoded by the codon pair corresponding to the anticodon pair present in the synthetic tRNA. The use of a synthetic tRNA aminoacylated with such a dipeptide would not only result in the intended suppression of the PTC and the production of a non-truncated protein, but in the production of a protein having the amino acid sequence of the wild-type protein.

In preferred embodiments, the synthetic transfer RNA of the invention has or comprises a) one of the sequences according to SEQ ID NO: 03-07, 09-17, 19-23, 25-30, 46-50 or 55-57, or b) a sequence having at least 90%, preferably at least 95%, 96%, 97%, 98% or 99% sequence identity with one of the sequences according to SEQ ID NO: 03-07, 09-17, 19-23, 25-30, 46-50 or 55-57, or c) a sequence of a) or b) above, wherein at least one of the nucleotides is replaced with a corresponding modified nucleotide. The term "replaced with a corresponding modified nucleotide" means that a unmodified nucleotide, e.g. a cytidine nucleotide (C), at a given position in a sequence, for example SEQ ID NO: 03, is replaced with a corresponding modified nucleotide, e.g. 2'-O-methylcytidine (cm), 3-methylcytidine (m3c) or 5-methylcytidine (m5c). The synthetic transfer RNA of the invention may, for example, have or comprise a sequence containing more than 10, 20 or 30 modified nucleotides.

In preferred embodiments, the synthetic transfer RNA comprises a) an anticodon loop having a sequence selected from the group of sequences consisting of CUCAGUUAGA (SEQ ID NO: 51), CUCAGUUAAA (SEQ ID NO: 52), ACUCAGUUAG (SEQ ID NO: 53), CUCAGUUAG, CUCAGUUAA, CUCAGUUAU, AUCAGUUAG, and ACUCAGUUA, or b) an anticodon loop having a sequence selected from the group of sequences consisting of CUCAGUUAGA (SEQ ID NO: 51), CUCAGUUAAA (SEQ ID NO: 52), ACUCAGUUAG (SEQ ID NO: 53), CUCAGUUAG, CUCAGUUAA, CUCAGUUAU, AUCAGUUAG, and ACUCAGUUA, wherein at least one of the nucleotides is replaced with a corresponding modified nucleotide. Each of the sequences CUCAGUUAGA (SEQ ID NO: 51), CUCAGUUAAA (SEQ ID NO: 52), ACUCAGUUAG (SEQ ID NO: 53), CUCAGUUAG, CUCAGUUAA, CUCAGUUAU, AUCAGUUAG, and ACUCAGUUA contains the sequence of an extended anticodon loop (see Table 3 below) with 10 (SEQ ID NO: 51-53) or 9 nucleotides. Each anticodon loop contains the anticodon tandem CAGUUA and the transfer RNAs according to these embodiments are particularly useful as a medicament for use in cystic fibrosis, for example for correcting a Y1092X mutation in CFTR.

It is particularly preferred that a G-C or C-G pair is positioned at the end of the anticodon stem in direction of the anticodon loop, that is that the nucleotides of the anticodon stem flanking the anticodon loop form a G-C or C-G pair.

For clarification, it is noted that the synthetic transfer RNA of the invention may or may not be synthesized to contain any modified nucleotides. The synthetic transfer RNA of the invention may thus not contain any modified nucleotide. However, after entering a cell, one or more nucleotides of that synthetic tRNA may nevertheless be modified within the cell by the cellular enzymatic machinery. Consequently, a synthetic tRNA of the invention, which has been designed, synthesized and administered without any modified nucleotide, may, in a living cell, contain one or more modified nucleotides due to modifications the cell has made to them. In fact, it is preferred that the synthetic tRNA of the invention is synthesized and also administered without containing any modified nucleotides and to leave any modifications to the cell.

If a synthetic tRNA of the invention is synthesized with modified nucleotides, such that the tRNA already contains modified nucleotides prior to administration, it is preferred that the tRNA of the invention contains one or more of the following modified nucleotides (Table 1):

TABLE 1

Figure 3:
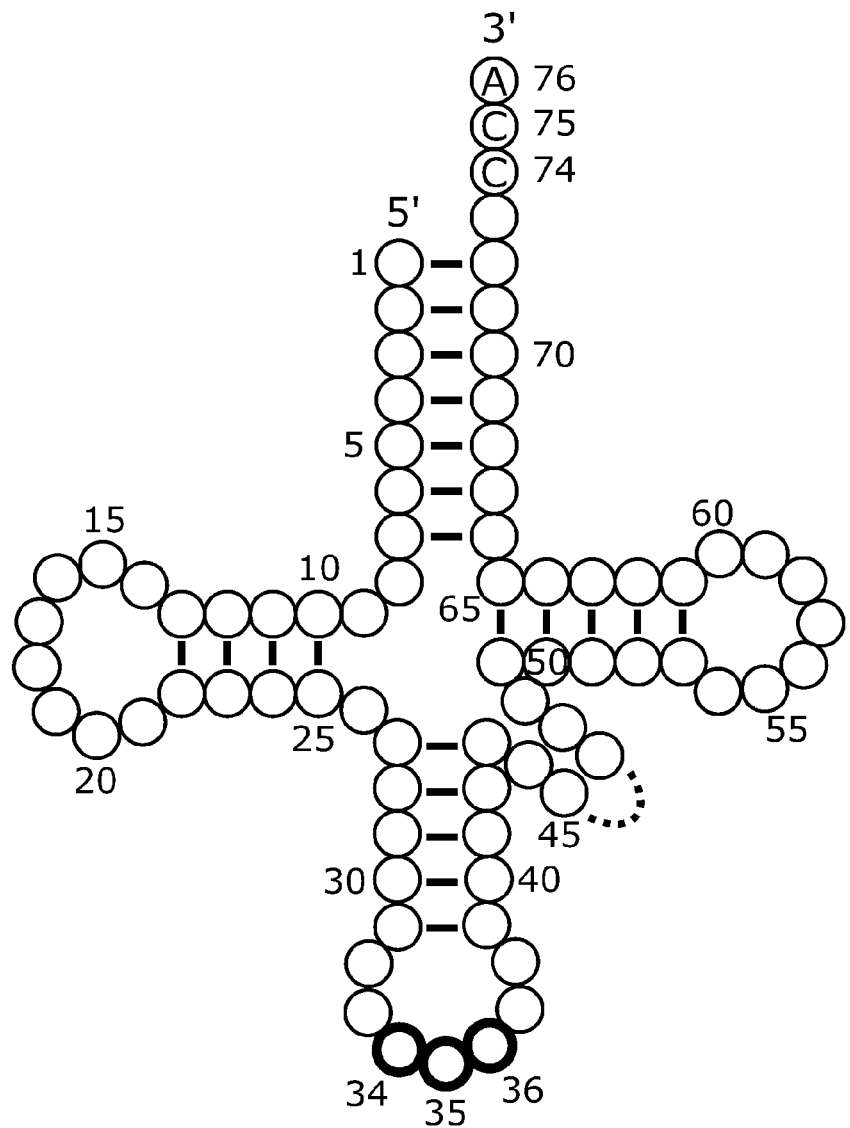

Possible modified nucleotides and positions within the tRNA (position numbering according to the specific tRNA numbering convention for a generalized "consensus" tRNA, see also FIG. 3)

| Position | Modification |
| --- | --- |
| 1 | Ψ |
| 4 | cm, am |
| 9 | m1g |
| 12 | ac4c |
| 16 | d |
| 17 | d |
| 18 | m2g |
| 20, 20a-b | d |
| 26 | m22g |
| 28 | Ψ |
| 29 | Ψ |
| 30 | Ψ |
| 32 | Ψ, 2'O-methylribose, cm |
| 34 | I, Ψ, m5c, cm, gm, 2'O-methylribose, q, mcm5u, ncm5u, ncm5um, mcm5s2u, |
| 35 | Ψ | m1g, 1-methylguanosine; am, 2'-O-methyladenosine; cm, 2'-O-methylcytidine; gm, 2'-O-methylguanosine; Ψ, pseudouridine; m2g, N2-methylguanosine; ac4c, N4-acetylcytidine; d, dihydrouridine; m22g, N2,N2-dimethylguanosine; m2g, N2-methylguanosine; I, inosine; m5c, 5-methylcytidine; mcm5u, 5-methoxycarbonylmethyluridine; mcm5s2u, 5-methoxycarbonyl-methyl-2-thiouridine; ncm5u, 5-carbamoylmethyluridine; ncm5 um, 5-carbamoyl-methyl-2'-O-methyluridine; q, queuosine; m5c, 5-methylcytidine.

In a further aspect the invention relates to the synthetic transfer RNA according to the first aspect of the invention for use as a medicament. The transfer RNA of the invention is especially useful for treating patients with a disease associated with a PTC causing the absence or dysfunction of a protein, in particular a disease at least partly caused by a nonsense mutation leading to premature cessation of the translation of an mRNA. Examples for diseases, in which the tRNA of the invention may advantageously be employed are cystic fibrosis, neurofibromatosis type 1, Duchenne muscular dystrophy or Hurler syndrome. Suitable compositions or means for delivering tRNAs to a cell are known, and include viral vectors such as viral vectors like adeno-associated virus (AAV)-based viral vectors, encapsulation in or coupling to nanoparticles.

In a preferred embodiment, the synthetic transfer RNA according to the invention are designed for use as a medicament for treating cystic fibrosis, and the two consecutive anticodon base triplets of the extended anticodon loop have the sequence CAGUUA. The synthetic transfer RNA may, for example, comprise an anticodon loop having a) a sequence selected from the group of sequences consisting of CUCAGUUAGA (SEQ ID NO: 51), CUCAGUUAAA (SEQ ID NO: 52), ACUCAGUUAG (SEQ ID NO: 53), CUCAGUUAG, CUCAGUUAA, CUCAGUUAU, AUCAGUUAG, and ACUCAGUUA, or b) having a sequence selected from the group of sequences consisting of CUCAGUUAGA (SEQ ID NO: 51), CUCAGUUAAA (SEQ ID NO: 52), ACUCAGUUAG (SEQ ID NO: 53), CUCAGUUAG, CUCAGUUAA, CUCAGUUAU, AUCAGUUAG, and ACUCAGUUA, wherein at least one of the nucleotides is replaced with a corresponding modified nucleotide. It is particularly preferred that the synthetic transfer RNA has an extended anticodon loop composed of 9 nucleotides. An example of a suitable tRNA having an extended 9nt nucleotide anticodon including the anticodon tandem CAGUUA is a transfer RNA with the sequence of SEQ ID NO: 6 or a sequence of SEQ ID NO: 6, wherein at least one of the nucleotides is replaced with a corresponding modified nucleotide.

The invention will be described by way of examples and the appended figures for illustrative purposes only.

FIG. 1 Schematic example of a synthetic tRNA of the invention and a targeted mRNA.

Figure 2:
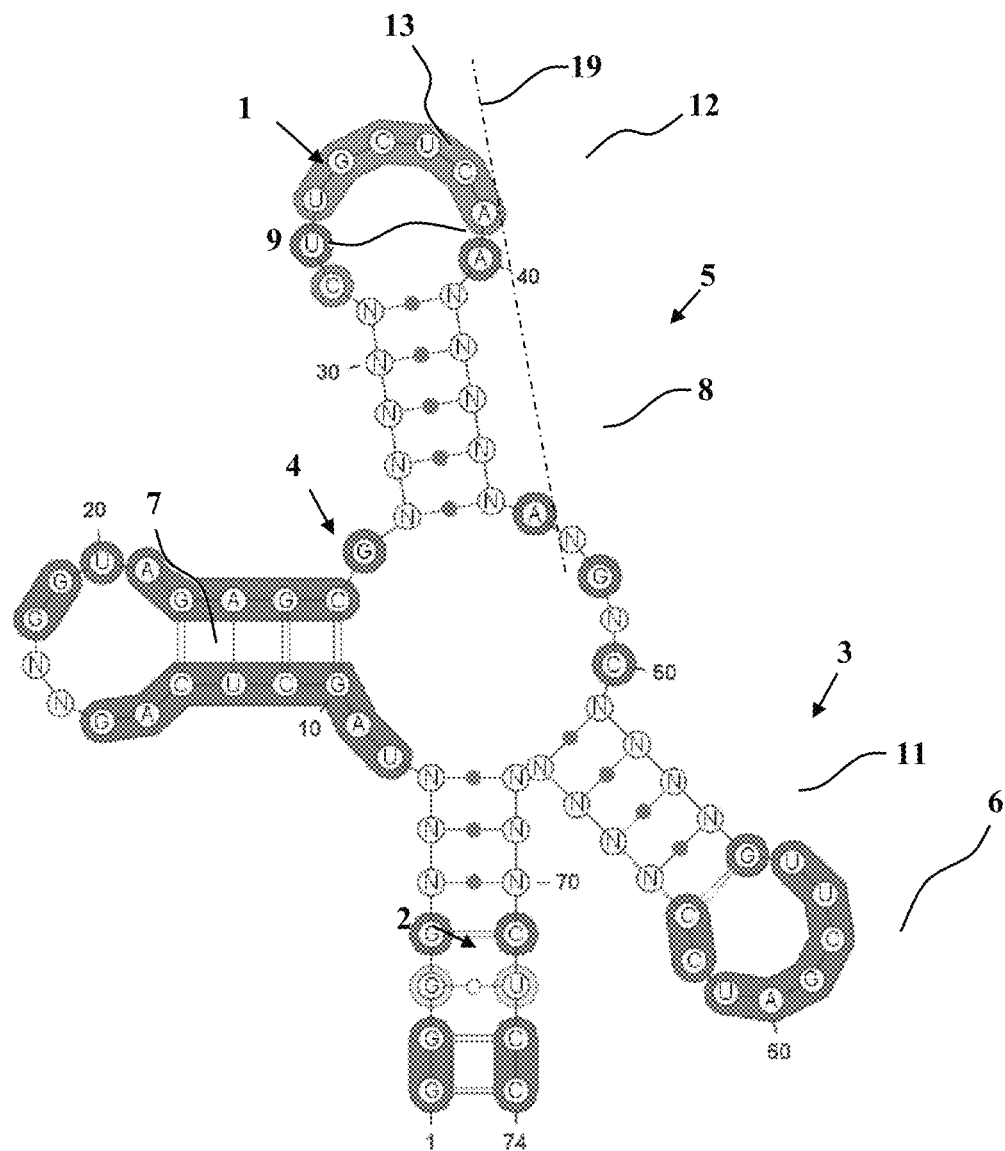

FIG. 2 Example embodiment of part of a synthetic Ala-tRNA of the invention. N=any nucleotide.

FIG. 3 Schematic drawing of a generalized "consensus" tRNA structure and its numbering according to tRNA numbering convention.

Figure 4:
Figure 5A:
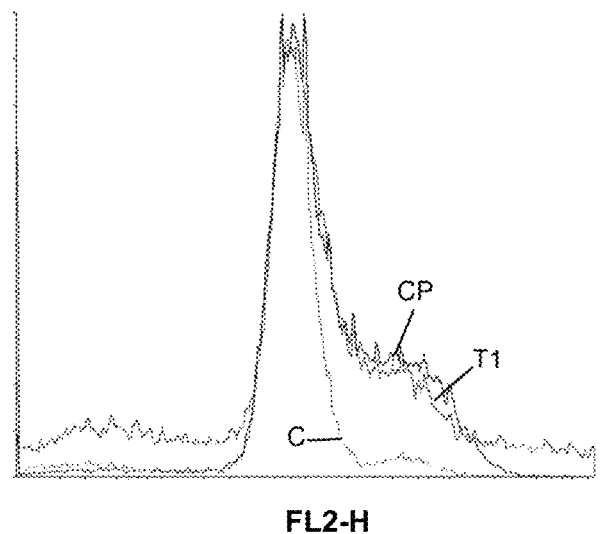
Figure 5A:
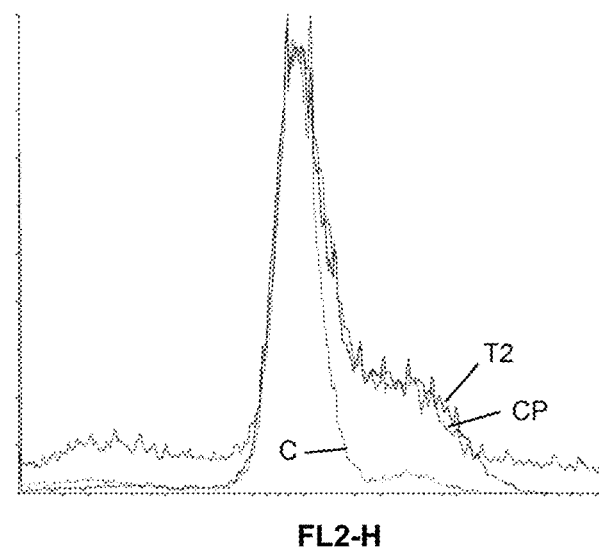
Figure 5B:
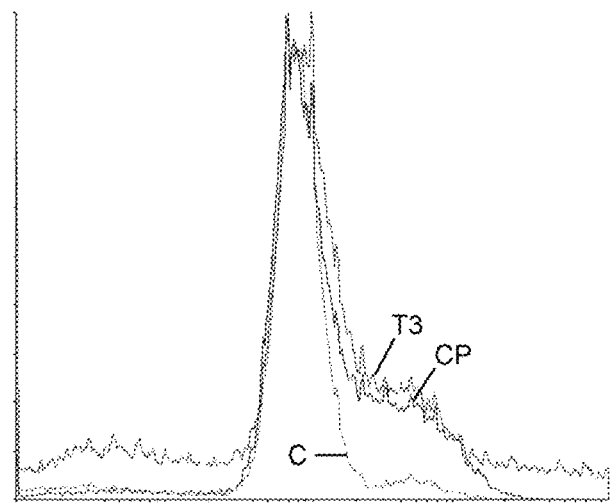
Figure 5B:
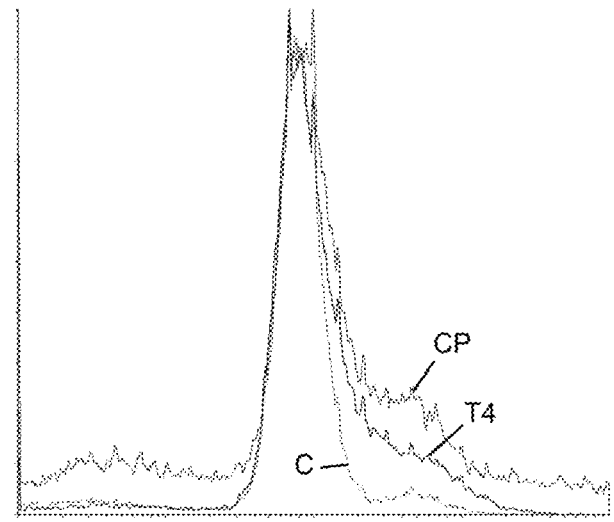
Figure 5C:
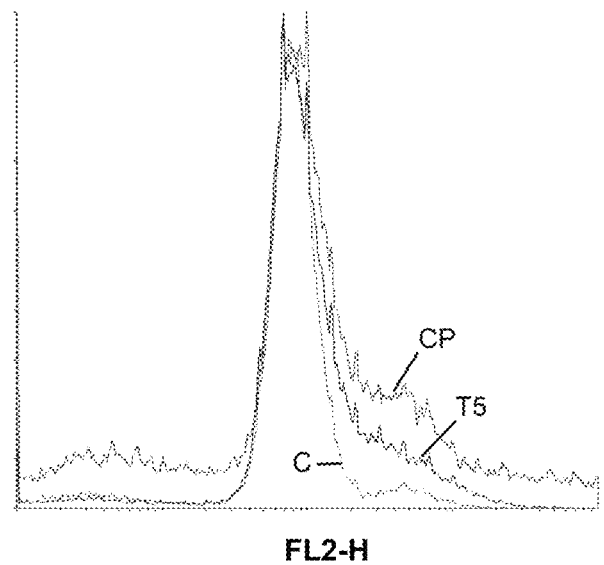
Figure 5C:
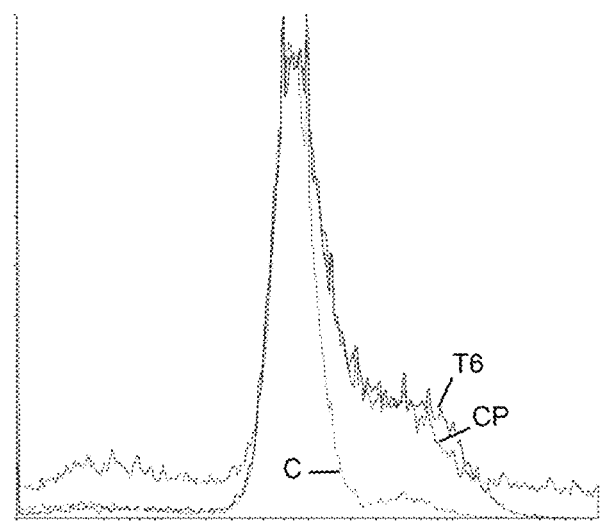
Figure 5D:
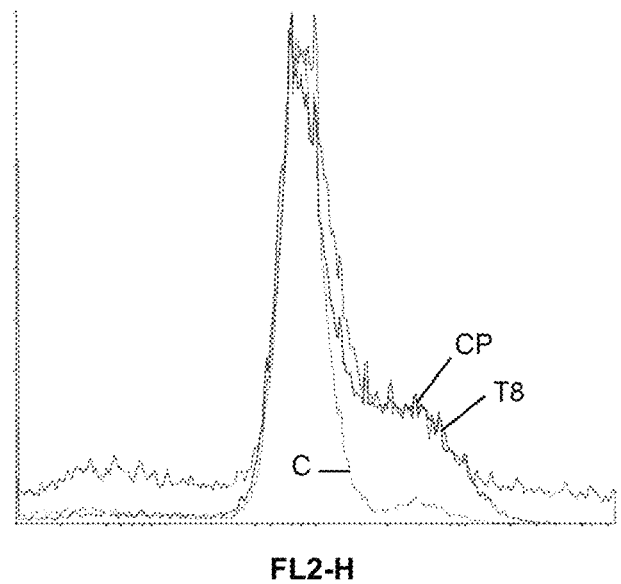
Figure 5D:
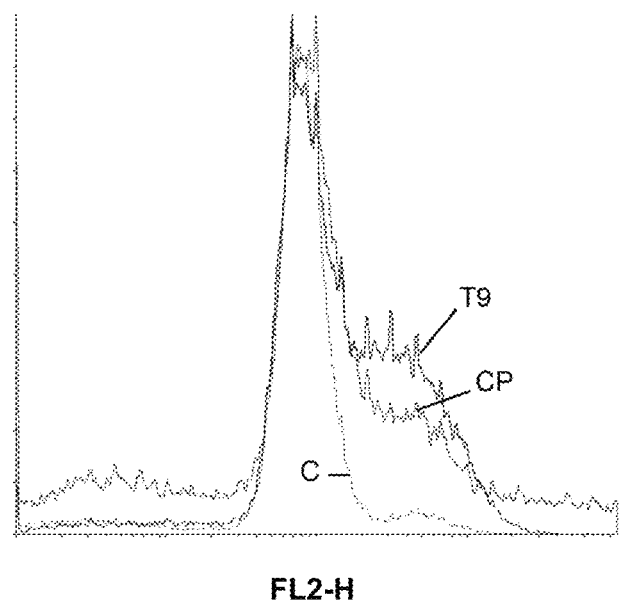

FIG. 4 Western blot showing GFP expression from a plasmid bearing a GFP coding sequence with a TGA stop codon using tRNA$^{Ala}$ variants with 3nt anticodon pairing to the TGA stop codon (upper part of figure). Control (lower part of figure): expression of housekeeping GAPDH gene. WT=wild-type GFP; Negative controls: 84=cells expressing the plasmid without the GFP gene; TGA=GFP with a stop codon without suppressor tRNA; NAV=empty pBST NAV2 vector.

FIG. 5 Results of experiments performed in HeLa cells for expression of the fluorescent mCherry protein from plasmid pECFP-C1 bearing an 11nt insert from the CFTR gene flanking the nonsense mutation Y1029X, sandwiched between CFP without stop codon and mCherry, using tRNA with extended anticodon loop. The mCherry expression was monitored by FACS detecting mCherry fluorescence. C=HeLa cells alone; CP=transformed pECFP1 bearing the reporter, no suppressor tRNA; T1-T6, T8-T9=with co-transformed pECFP1 bearing the reporter and corresponding suppressor tRNA with extended anticodon loop (T1-T6, T8-T9=tRNA-L1-6, tRNA-L8-9).

FIG. 1 shows a schematic example of a synthetic tRNA of the invention and a targeted mRNA. The synthetic tRNA 1 of the invention is composed of tRNA nucleotides 11 and has the common cloverleaf structure of natural tRNA comprising an acceptor stem 2 with the CCA tail 10, a T arm 3 with the T$_\psi$C loop 6, a D arm 4 with the D loop 7 and an anticodon arm 5 with a five nucleotide stem portion 8 and the anticodon loop 9. An amino acid 14 is bound to the CCA tail 10 of the acceptor stem 2. The extended anticodon loop 9 consists of nine nucleotides 11 and contains two consecutive anticodon base triplets 12, 13. The first anticodon base triplet 12 (hatched circles) is able to base-pair to a first codon base triplet 17 (also hatched) on a targeted mRNA 15 composed of mRNA nucleotides 16. The second anticodon base triplet 13 (solid black circles) is able to base-pair to a second codon base triplet 18 (also solid black) on the mRNA 15. The first codon base triplet 17 may be a premature termination codon (PTC) and the second codon base triplet 18 may code for an amino acid, e.g. alanine, or vice versa. A variable loop often found in naturally occurring tRNA between the T arm and the anticodon arm is missing here.

EXAMPLES

In silico design of a synthetic tRNA of the invention.

Unless otherwise indicated all sequences are written in the 5'-3' direction. In all sequences, if a minus sign (hyphen, "-") is used, this is for clarity only and does not refer to a physical nucleotide. It is a purely typographical convention to align sequences on a page. Further, unless expressly stated otherwise, bases are simply numbered sequentially, not according to the tRNA convention mentioned above.

First of all, a naturally occurring human Leu tRNA was modified only in its anticodon loop.

Original human tRNA-Leu (M2GAA) (genbank accession X04700.1; anticodon underlined), SEQ ID NO: 01:

```
GUCAGGAUGGCCGAGUGGUCUAAGGCGCCA

GACUNAAGUUCUGGUCUCCGGAUGGAGCGU

GGGUUCGAAUCCCACUUCUGACACCA
```

The above naturally occurring tRNA contains, when isolated from a cell, modified bases in its sequence, which are represented in the above sequence by N or the corresponding unmodified bases. As an example, N at position 35 (corresponding to position 34 according to the specific tRNA numbering convention mentioned above) represents m22g (2,2-dimethylguanosine).

tRNAs were designed in order to be able to correct a mutation in CFTR leading to a stop codon (X) next to a codon coding for leucine (leu, L):

5'-CAGUUA-3' 6nt anticodon pair complementary to the following codons:

3'-GUCAAU-5' mRNA sequence (5'-stop-leu-3') shall be recognized

In addition to a tRNA based on the natural tRNA modified in only one base in the normal anticodon, five tRNAs (designs 1.1 to 1.5) with an extended anticodon loop were designed. As mentioned above, modified nucleotides may or may not also be present in the modified sequences, i.e. the sequences given below for the designed tRNAs may contain one or more corresponding modified nucleotides instead of the unmodified bases. The number and kind of modified nucleotides may be the same or different from the ones in the natural tRNA template. Any unmodified nucleotide in a sequence for a synthetic tRNA of the invention may thus be replaced with a corresponding modified nucleotide. The symbols A, C, G or U in the below sequences for designed tRNAs may therefore represent an unmodified or any corresponding modified base. An A in a sequence may, for example, represent an adenine nucleotide (A) or a corresponding modified nucleotide, e.g. 1-methyladenosine (m1a). When synthesized in vitro, the tRNAs are preferably unmodified, but may be subsequently modified chemically and/or enzymatically in vitro. Once introduced or incorporated in a cell, the tRNAs, whether in vitro synthesized with unmodified or modified nucleotides, may be modified by the cell.

```
tRNA-Leu (UAA) with substituted base U at
position 35 (34 according tRNA numbering
convention),
                                SEQ ID NO: 02
GUCAGGAUGGCCGAGUGGUCUAAGGCGCCAGACUUAAGUUCUG

GUCUCCGGAUGGAGCGUGGGUUCGAAUCCCACUUCUGACACCA

Design 1.1: tRNA-Leu CAGUUA anticodon pair
(underlined), 10nt anticodon loop,
                                SEQ ID NO: 03
GUCAGGAUGGCCGAGUGGUCUAAGGCGCCAGACUCAGUUAGUU

CUGGUCUCCGGAUGGAGCGUGGGUUCGAAUCCCACUUCUGACA

CCA
```

-continued

Design 1.2: tRNA-Leu-CAGUUA anticodon,
9 nt anticodon loop (deleted C33, compared to
design 1.1),
SEQ ID NO: 04
GUCAGGAUGGCCGAGUGGUCUAAGGCGCCAGAUCAGUUAGUUC

UGGUCUCCGGAUGGAGCGUGGGUUCGAAUCCCACUUCUGACAC

CA

Design 1.3: tRNA-Leu-CAGUUA anticodon,
9nt anticodon loop (deleted U34, compared to
design 1.1),
SEQ ID NO: 05
GUCAGGAUGGCCGAGUGGUCUAAGGCGCCAGACCAGUUAGUUCU
GGUCUCCGGAUGGAGCGUGGGUUCGAAUCCCACUUCUGACACCA Design 1.4: tRNA-Leu-CAGUUA anticodon,
9nt anticodon loop (deleted G41, compared to
design 1.1),
SEQ ID NO: 06
GUCAGGAUGGCCGAGUGGUCUAAGGCGCCAGACUCAGUUAUUCU

GGUCUCCGGAUGGAGCGUGGGUUCGAAUCCCACUUCUGACACCA

Design 1.5: tRNA-Leu-CAGUUA anticodon,
9 nt anticodon loop (deleted U42, compared to
design 1.1),
SEQ ID NO: 07
GUCAGGAUGGCCGAGUGGUCUAAGGCGCCAGACUCAGUUAGUCU

GGUCUCCGGAUGGAGCGUGGGUUCGAAUCCCACUUCUGACACCA

The optimal anticodon loop length was 9nt.

Starting from design 1.4 (CAGUUA anticodon, 9nt anticodon loop (deleted G41)), further Leu tRNA (with 6nt anticodon pair) were designed with less similarity to the naturally occurring tRNAs, based on the crystal structure from a tRNA-Leu from *Thermus thermophilus*:

tRNA-Leu-CAG from *Thermus thermophilus* (3nt anticodon, sequence is from RCSB Protein Data Bank identifier 2bte.b; any modified nucleotides present in the sequence are represented by their respective unmodified nucleotides).

SEQ ID NO: 08
GCCGGGGUGGCGGAAUGGGUAGACGCGCAUGACUCAGGAU

CAUGUGCGCAAGCGUGCGGGUUCAAGUCCCGCCCCCGGCA

CCA

This resulted in the design of the following tRNA-Leu-CAGUUA (Leu-Stop) having 6nt anticodon pairs based on design 1.4 (9nt anticodon loop) above:

Design 2.1
(SEQ ID NO: 09):
GGCAGGCUGAGGGAGAUGGUCAACCUAGCCAGCUCAGUUAGCUGGCUCU

CCGGAUGGAGCGUGGCUUCGAAUGCCACGCCUGCCACCA
Design 2.2
(SEQ ID NO: 10):
GACAGGCUGAGGGAGAUGGUCAACCUAGCAGCCUCAGUUAGGCUGCUCU CCGGAUGGAGCGUGGCUUCGAAUGCCACGCCUGUCACCA
Design 2.3
(SEQ ID NO: 11):
GCCAGCCUGAGGGAGAUGGUCAACCUAGCCAGCUCAGUUAGCUGGCUCU CCGGAUGGAGCGUGGCUUCGAAUGCCACGGCUGGCACCA
Design 2.4
(SEQ ID NO: 12):
GGCAGCCUGAGGGAGAUGGUCAACCUAGCAGCCUCAGUUAGGCUGCUCU

CCGGAUGGAGCGUGGCUUCGAAUGCCACGGCUGCCACCA

-continued

Design 2.5
(SEQ ID NO: 13):
GCCAGCCUGAGGGAGAUGGUCAACCUAGGUGCCUCAGUUAGGCACCUCU

CCGGAUGGAGCGUGGCUUCGAAUGCCACGGCUGGCACCA
Design 2.6
(SEQ ID NO: 14):
GCCAGCCUGAGGGAGAUGGUCAACCUACUGGACUCAGUUAGUCCAGUC UCCGGAUGGAGCGUGGCUUCGAAUGCCACGGCUGGCACCA
Design 2.7
(SEQ ID NO: 15):
GCCAGCCUGAGGGAGAUGGUCAACCUACCGGACUCAGUUAGUCCGGUC UCCGGAUGGAGCGUGGCUUCGAAUGCCACGGCUGGCACCA
Design 2.8
(SEQ ID NO: 16):
GCCAGCCUGAGGGAGAUGGUCAACCUACCUGCCUCAGUUAGGCAGGUCU CCGGAUGGAGCGUGGCUUCGAAUGCCACGGCUGGCACCA
Design 2.9
(SEQ ID NO: 17):
GCCAGGCUGAGGGAGAUGGUCAACCUAGCUCACUCAGUUAGUGAGCUCU

CCGGAUGGAGCGUGGCUUCGAAUGCCACGCCUGGCACCA

Again, any modified nucleotide present in the natural sequence taken as a template for the design of the synthetic tRNAs may or may not also be present in the designed sequences. The designed tRNAs above thus may or may not contain one or more corresponding modified nucleotides instead of the unmodified bases.

For the correction of a further stop mutation (at position 553) in the CFTR gene (R553X), mutating the wild-type codon CGA coding for arginine (R), and flanked by codons coding for glutamine (Q) and alanine (A), to a stop codon (TGA on gene level)

CAA CGA GCA (wildtype nucleotide sequence)

Q   R   A   (wildtype amino acid sequence)

CAA TGA GCA (mutated nucleotide sequence)

Q   X   A   (mutated nucleotide sequence)

the tRNA was designed to have a 6nt anticodon pair (UGCUCA) and to be aminoacylated with alanine (Ala, A), i.e. to have the identity of a Ala-tRNA. Ala is the amino acid following the stop codon (in 3' direction of the mRNA).

The goal was to design a tRNA that would be able to read through a stop codon and deliver a Ala to the protein being translated (read through a premature stop codon caused by mutation which would otherwise lead to a truncated protein).

5'-UGCUCA-3' 6nt anticodon pair complementary to the two codons below 3'-ACGAGU-5' mRNA sequence (5-Stop-Ala-3'; XA) to be recognised Similar to the Leu-tRNAs at first a natural human Ala-tRNA was minimally changed, i.e. only in the anticodon loop. Again, any modified nucleotides in the sequence are represented by their unmodified equivalents, and the synthetic tRNAs designed based on the natural tRNA may or may not contain all or part of the modified nucleotides of the natural sequence. The designed tRNAs may also contain more or other modified nucleotides than the ones present in the naturals sequence and/or at another position.

```
tRNA-Ala-AGC
(SEQ ID NO: 18), without free 3' end ACCA:
GGGGAAUUAGCUCAAAUGGUAGAGCGCUCGCUUAGCAUGCGAG

AGGUAGCGGGAUCGAUGCCCGCAUUCUCC

Design 3.1 (10 nt anticodon loop)
(SEQ ID NO: 19)
GGGGAAUUAGCUCAAAUGGUAGAGCGCUCGCUUUGCUCAAUGC GAGAGGUAGCGGGAUCGAUGCCCGCAUUCUCCACCA
Design 3.2 (9 nt anticodon loop)
(SEQ ID NO: 20)
GGGGAAUUAGCUCAAAUGGUAGAGCGCUCGCUUGCUCAAUGCG

AGAGGUAGCGGGAUCGAUGCCCGCAUUCUCCACCA

Design 3.3 (9 nt anticodon loop)
(SEQ ID NO: 21)
GGGGAAUUAGCUCAAAUGGUAGAGCGCUCGCUUUGCUCAUGCG

AGAGGUAGCGGGAUCGAUGCCCGCAUUCUCCACCA

Design 3.4 (9 nt anticodon loop)
(SEQ ID NO: 22)
GGGGAAUUAGCUCAAAUGGUAGAGCGCUCGCUUUGCUCAAGCG

AGAGGUAGCGGGAUCGAUGCCCGCAUUCUCCACCA
```

Experiments showed that both 10 nt and 9nt anticodon loop tRNAs formed a secondary structure corresponding to naturally occurring tRNA, and the single-stranded CCA tails were intact. All tRNAs could be aminoacylated.

Starting from design 1.4 of the Ala-tRNA further Ala-tRNA were designed, such that the tRNA body did not correspond to the natural human tRNA.

```
tRNA-Ala-UGCUCA-design 3.4
                                     (SEQ ID NO: 22)
GGGGAAUUAGCUCAAAUGGUAGAGCGCUCGCUUUGCUCAAGCG

AGAGGUAGCGGGAUCGAUGCCCGCAUUCUCCACCA
```

A generalized secondary structure of the designed tRNA is depicted in FIG. 2 (sequence shown in the figure given in SEQ ID NO: 24). Reference numbers correspond to those used in FIG. 1. The free 3' end including the CCA tail portion is not shown. Also shown in FIG. 2 is the asymmetric arrangement of the two consecutive anticodon base triplets ("anticodon tandem") 13 in the extended anticodon loop 9 in relation to an imaginary symmetry axis 19 longitudinally traversing through the stem 8 of the anticodon arm 5 and extended in the direction of the anticodon loop 9. The anticodon tandem 13 is arranged offset towards the 3' end of the tRNA.

The sequence of the tRNA based on the Ala-tRNA and having a 9nt anticodon loop with a 2×3 nt anticodon (FIG. 2) and including the 3' end portion is as follows (SEQ ID NO: 23):

```
GGGGNNNUAGCUCAGNNGGUAGAGCGNNNNNCUUGCUCAANN

NNNANGNCNNNNGUUCGAUCCNNNNNNNCUCCACCA
```

As already mentioned in connection with other synthetic tRNAs of the invention, the symbols G, C, A or U may represent the unmodified or any corresponding modified base. The above designed tRNA may thus contain one or more modified nucleotides.

N stands for any of the bases A, C, G or U, or any modified base, given that the base doesn't violate the base pairing as given in FIG. 2. The allowed base pairs are G-C, C-G, A-U, U-A, and wobble base pairs like G-U, U-G, I-U, U-I, I-A, A-I and I-C, C-I.

FIG. 3 depicts an example of a tRNA numbered according to the conventional numbering applied to a generalized "consensus" tRNA, beginning with 1 at the 5' end and ending with 76 at the 3' end. In such a "consensus" tRNA the nucleotides of the natural anticodon triplet is always at positions 34, 35 and 36, regardless of the actual number of previous nucleotides. Other than the tRNA shown here a tRNA may, for example, also contain additional nucleotides between positions 1 and 34, e.g. in the D loop. Additional nucleotides may be numbered with added alphabetic characters, e.g. 20a, 20b etc. Modified nucleotides, as e.g. listed in Table 1 above, may be present in the sequence.

Optimizing the tRNA body sequence for efficient read-through

Different tRNAs (n1-n6, SEQ ID NO: 33-38) based on a natural human tRNA$^{Ala}$ were synthesized in vitro. All tRNAs had the same non-extended anticodon loop containing an anti-stop-codon, that is a anticodon complementary to a stop codon. For this purpose, oligonucleotides having the tRNA sequences were ligated with the T7 promotor sequence (SEQ ID NO: 32), and the tRNAs were produced in a T7-based in vitro transcription system. Subsequently, the tRNAs were purified using polyacrylamide gel electrophoresis (PAGE).

The template for T7-promoter driven transcription of designed tRNAs was generated by annealing and primer extension of two overlapping DNA oligonucleotides (commercially available) covering the whole length of each tRNA including the T7 promoter sequence (5'-TAATACGACTCACTATA-3', SEQ ID NO: 32). Both oligonucleotides were denatured for 2 min at 95° C. and annealed in their partial overlapping area by incubating for 3 min at room temperature in 0.2 M Tris-HCl (pH 7.5). To fill up the DNA templates, that is to extend the nucleotide chains and form fully double-stranded DNA (dsDNA), 0.4 mM dNTPs, 4 U/µL RevertAid Reverse Transcriptase (RT, Thermo Fisher) and 1x RT buffer were added to the annealed oligonucleotides and reactions were incubated for 40 min at 37° C. The DNA template was purified with phenol/chloroform.

The in vitro T7-driven transcription of tRNAs was performed in two different scales, dependent on the follow-up experiment. For in vitro analysis of the tRNA integrity we used 1 µg template DNA in 40 mM Tris-HCl (pH 7.0, containing 6 mM $MgCl_2$, 10 mM DTT, 10 mM NaCl, 2 mM spermidine, 2 mM NTPs, 1.25-5 mM GMP) and 30 U T7 RNA polymerase (Thermo Fisher) overnight at 37° C. tRNAs were precipitated with ethanol, separated on 10% denaturing polyacrylamide gels and eluted overnight at 4° C. with 50 mM potassium acetate (KOAc), 200 mM KCl pH 7.0 at constant shaking (1000 rpm). tRNAs were recovered by ethanol precipitation and resuspended in DEPC-$H_2O$ (DEPC=diethylpyrocarbonate).

For transfections into eukaryotic cells since larger amounts are needed, 20 µg template were mixed with 100 mM of each NTP, 100 mM GMP, 1.2 U T7 RNA polymerase (Thermo Fisher) in 1× transcription buffer and incubated overnight at 37° ° C. The tRNAs were purified as described above, resuspended in DEPC-$H_2O$ and stored at −80° C. for further use.

In order to check the folding and the integrity of the CCA ends, the tRNA were incubated with a fluorophore-labelled oligonucleotide in a ratio of 1:1 for 1 h at 25° C., and subsequently separated via PAGE. Fluorescent labelling was performed by ligating a Cy3-labeled RNA/DNA stem-loop oligonucleotide to the common 3'-NCCA ends of tRNAs as described earlier (Czech A, Wende S, Mörl M, Pan T, Ignatova Z, 2013, Reversible and rapid transfer-RNA deactivation as a mechanism of translational repression in stress, PLOS Genet. 2013 9(8):e1003767. doi: 10.1371/journal.pgen. 1003767). The tRNAs labelled with the fluorescing oligonucleotide could be visualised in a fluorescence imager and migrate slower than non-labelled tRNAs. The designed tRNAs n1 to n5 were compared to controls: native tRNA$^{Ala}$ (GGC) (SEQ ID NO: 41), native tRNA$^{Ala}$(UGC) (SEQ ID NO: 42), native tRNA$^{Ala}$ in which only the anticodon was replaced with an anti-stop codon tRNA$^{Ala}$(UCA), SEQ ID NO: 41, and n6 (no tertiary interactions in the design), SEQ ID NO:38. The ratio of labelled (ligated) to non-labelled (non-ligated) tRNAs gives the ligation efficiency (table 2).

TABLE 2

Ligation efficiency of designed tRNA compared to controls.

| tRNA species | SEQ ID NO: | Ligation efficiency |
|---|---|---|
| tRNA$^{Ala}$ (n1) | 33 | ~20% |
| tRNA$^{Ala}$ (n2) | 34 | ~15% |
| tRNA$^{Ala}$ (n3) | 35 | ~15% |
| tRNA$^{Ala}$ (n4) | 36 | ~17% |
| tRNA$^{Ala}$ (n5) | 37 | ~14% |
| tRNA$^{Ala}$ (n6) | 38 | ~16% |
| tRNA$^{Ala}$ (GGC) | 39 | ~16% |
| tRNA$^{Ala}$ (UGC) | 40 | ~17% |
| tRNA$^{Ala}$ (UCA) | 41 | ~14% |

The designed tRNAs were tested for correct folding and aminoacylation. tRNA folding and aminoacylation reactions were performed using 1 mM alanine and 1 µM of E. coli alanyl-tRNA synthetase. Aminoacylated tRNAs were precipitated with ethanol and directly dissolved in 2× acidic RNA loading dye (0.1 M NaOAc pH 4.8, containing 8M urea, 5% glycerol, 0.025% bromophenol blue, 0.025% xylene cyanol FF). Charged and uncharged tRNA fractions were separated on denaturing acidic PAGE (6.5%, 8 M urea, 0.1M NaOAc pH 5.0) at 4° C. tRNAs were visualized by SYBR® gold (Invitrogen) staining.

All in-vitro-designed tRNAs were aminoacylated to a degree similar to the native tRNA$^{Ala}$ except n2, which was not acylated.

A GFP readthrough assay was used to test whether designed tRNA containing a stop codon in the non-extended anticodon loop are translationally active or not. For this purpose, a translational system was used comprising the coding sequence of green fluorescent protein (GFP). The codon coding for the 28$^{th}$ amino acid in the GFP was replaced with a stop codon. With the stop codon, GFP is normally not expressed. If, however, a designed suppressor tRNA having an anticodon complementary to the stop codon pairs to this codon, GFP is expressed. Its expression can be detected by either a fluorescence activated cell sorting (FACS) apparatus or by Western blot.

It is to be noted that, in this assay, only one codon (triplet) in the GFP coding sequence was replaced with a stop codon in order to avoid the green fluorescent protein not folding. Nevertheless, the method is fast and can be used to determine the effects of modifications to the tRNA body (see below). For the further experiments, the anticodon loop of the tRNAs was not changed. Only the natural anticodon of Ala-tRNA was converted into an antistop codon.

Two systems were used: a) an in vitro translation system and b) expression in E. coli. In case of the in vitro translation system expression was measured by Western blot, in case of the use of E. coli, Western blot and occasionally FACS was applied. Since the designed tRNAs share the same architecture for translation and loading, their translational ability is independent of the system and they can be used for in vitro expression as well as in vivo expression in prokaryotes or eukaryotes.

For in vitro translation a commercially available system was used (Promega). In the in vitro translation system, the tRNA was first transcribed in vitro and added 1:10 to the plasmid DNA (GFP with PTC, i.e. stop codon). After 1 hr at 30° C., the reaction mixture was separated by PAGE and an aliquot was detected with GFP antibodies.

For the in vivo expression system, designed tRNAs were cloned into the pBST NAV2 vector under the lpp promoter (Meinnel T, Blanquet S J, 1995, Maturation of pre-tRNA (fMet) by Escherichia coli RNase P is specified by a guanosine of the 5'-flanking sequence, Biol Chem. 270: 15908-14). XL1-blue cells were co-transformed with pBAD33 plasmid bearing wildtype GFP or PTC GFP variants and tRNA-expressing pBST NAV2 vector and grown in LB medium at 37° C. Growth curves were recorded at OD600 nm. The expression of the GFP variants was induced at OD$_{600\ nm}$-0.4 with 0.05% L-arabinose. Cells were harvested at OD$_{600\ nm}$=1.0 and the GFP expression was monitored by immunoblotting using anti-GFP antibodies. The expression is compared to the housekeeping GAPDH gene. In parallel, cells were harvested, washed and resuspended in PBS buffer and subjected to fluorescence measurements in bulk using a microtiter plate reader (Tecan GENios) with 485 nm excitation and 535 nm emission filter, or subjected to flow cytometry on FACS Calibur (Becton Dickinson).

For the readthrough assay, designed variants of the n1 tRNA$^{Ala}$ variant having an anti-stop-codon in its non-extended anticodon loop to pair to the TGA stop codon were used, which were further modified in their T-stem or in both their T-stem and D arm in order to determine the effect of modifications to the T-stem and D arm for promoting translation readthrough. The in vivo translation system described above was used for this purpose. Translation of Glyceraldehyde 3-phosphate dehydrogenase (GAPDH) and wild-type GFP (without PTC) were used as a control.

The tRNA modified in their T-stem were designated TS1 (SEQ ID NO: 42) and TS2 (SEQ ID NO: 43), the tRNA modified in their T-stem and additionally in their D arm were designated DTS1 (SEQ ID NO: 44) and DTS2 (SEQ ID NO: 45)

```
TS1
(SEQ ID NO: 42); underlined: anticodon;
bold: T-stem
GGGGCGGUAGCUCAGAAGGGAGAGCAGCGGCCUUCAGAGCC

GCGAGACUGCCCUUCGAUUGGGCACCGCUCCACCA

TS2
(SEQ ID NO: 43); underlined: anticodon;
bold: T-stem
GGGGCGGUAGCUCAGAAGGGAGAGCAGCGGCCUUCAGAGCC

GCGAGACAGGGGUUCGAUUCCCCUCCGCUCCACCA
```

-continued

```
DTS1
(SEQ ID NO: 44); underlined: anticodon;
bold: T-stem, italics = D arm
GGGGCGGUAGCGCAGCCUGGUAGCGCAGCGGCCUUCAGAGC

CGCGAGACUGCCCUUCGAUUGGGCACCGCUCCACCA

DTS2
(SEQ ID NO: 45); underlined: anticodon;
bold: T-stem, italics = D arm
GGGGCGGUAGCGCAGCCUGGUAGCGCAGCGGCCUUCAGAGC

CGCGAGACAGGGGUUCGAUUCCCCUCCGCUCCACCA
```

The tRNA TS2 (SEQ ID NO: 43) modified to have a T-stem nucleotide sequence of AGGGG (positions 49 to 53, numbering according to tRNA convention) and CCCCU (positions 61 to 65, numbering according to tRNA convention), i.e. the following T-stem structure

```
                3'-UCCCC-5'

5'-AGGGG-3'
``` showed readthrough (see TS2 in FIG. 4). It is to be noted that the T-loop would be between the G at the 3' end of the AGGGG sequence and the C at the 5' end of the UCCCC sequence. The corresponding T arm would thus have the structure 5'-AGGGG-(T-Loop)-CCCCU-3'.

In order to test the effect of a modification of other structures of the tRNA body on translation readthrough, the above-described tRNA with modified T-stem (TS1 and TS2) were further modified in that the D-arm was replaced with the D-region of the *E. coli* tRNA$^{Pro}$. The modified tRNA were designated DTS1 (SEQ ID NO: 44) and DTS2 (SEQ ID NO: 45). The tRNA DTS2 (SEQ ID NO: 45) modified in its T-stem and its D arm promoted a higher readthrough than the tRNA only modified in its T-stem (see DTS2 in FIG. 4).

Using tRNA$^{Leu}$ for correcting Y1092X mutation in CFTR

A modified tRNA$^{Leu}$ was used to correct the Y1092X mutation in CFTR, resulting from a change of C at position 3276 to A or G in the CFTR gene:

```
Natural CFTR sequence:
TTGTACCTG

Mutated sequence (C3276A):
TTGTAACTG
```

The natural tRNA$^{Leu}$ (see SEQ ID NO: 1) was used as a template in order to design modified tRNAs having an anticodon tandem of the sequence CAGUUA in their anticodon loop. The designed tRNAs could be aminoacylated in vivo with leucine (Leu). The identity elements for the Leucyl-tRNA synthetase were unchanged.

To test whether the designed tRNAs would function in a translation system, a sandwich construct was used, comprising a short sequence containing the mutated CFTR sequence (UUGUAACUG) sandwiched between two fluorescent proteins, namely yellow fluorescent protein (CFP) and mCherry. CFP had no stop codon and was extended with an 11 nucleotide long insert being a piece of the gene to be repaired (here CFTR around the mutation Y1029X) and containing a stop codon. The tRNA anticodon loops were correspondingly extended in order to pair to six consecutive nucleotides. After the insert containing a stop codon, mCherry was cloned without an initial codon (coding for the amino acid Met), so that no independent translation of mCherry could take place. In the biciscronic reporter system, CFP is always expressed up to the stop codon of the mutation, while mCherry is only expressed when readthrough takes place. This expression can be detected by either a fluorescence activated cell sorting (FACS) apparatus or by Western blot. A plasmid without insert was used as a control.

For studying tRNA suppression in Hela cells, HeLa cells were maintained at 37° ° C., 5% $CO_2$ in DMEM media supplemented with 10% FBS (fetal bovine serum) and 1% glutamine (GIBCO). One day prior to co-transfection ~200,000 cells were seeded in 6-well plates. The transfection mix included 600 ng reporter plasmid encoding CFP-PTC-mCherry cloned in the pECGFP-C1 backbone, 150 ng suppressor tRNAs, 5 μl Lipofectamine 2000 (ThermoFisher 679 Scientific, USA) in 200 μL Optimem medium (Gibco). Cells were incubated with transfection mix for 6 hours. Thereafter, the medium was exchanged with fresh medium. After 24 hours, the cells were washed with 1×PBS and analysed by FACS Calibur (Becton Dickinson). Analysis was performed by counting 50000 events, FSC Voltage E00 and 1.60 Amp Gain and using 400 nm wavelength for CFP and 520 nm for mCherry detection.

The following tRNA variants (anticodon tandem underlined) were tested (see also Table 3):

```
tR-L1
                                      (SEQ ID NO: 46)
GUCAGGAUGGCCGAGUGGUCUAAGGCGCCACCUCAGUUAGAGUCU

GGUCUCCGGAUGGAGCGUGGGUUCGAAUCCCACUUCUGACACCA tR-L2
                                      (SEQ ID NO: 47)
GUCAGGAUGGCCGAGUGGUCUAAGGCGCCACCUCAGUUAAAGUC

UGGUCUCCGGAUGGAGCGUGGGUUCGAAUCCCACUUCUGACACCA tR-L3 = tRNA Leu Design 1.1
                                       (SEQ ID NO: 3)
GUCAGGAUGGCCGAGUGGUCUAAGGCGCCAGACUCAGUUAGUUC

UGGUCUCCGGAUGGAGCGUGGGUUCGAAUCCCACUUCUGACACCA tR-L4
                                      (SEQ ID NO: 48)
GUCAGGAUGGCCGAGUGGUCUAAGGCGCCACCUCAGUUAGGUCU

GGUCUCCGGAUGGAGCGUGGGUUCGAAUCCCACUUCUGACACCA tR-L5
                                      (SEQ ID NO: 49)
GUCAGGAUGGCCGAGUGGUCUAAGGCGCCACCUCAGUUAAGUC
UGGUCUCCGGAUGGAGCGUGGGUUCGAAUCCCACUUCUGACAC
CA
tR-L6
                                      (SEQ ID NO: 50)
GUCAGGAUGGCCGAGUGGUCUAAGGCGCCACCUCAGUUAUGUC

UGGUCUCCGGAUGGAGCGUGGGUUCGAAUCCCACUUCUGACAC

CA
tR-L8 = tRNA Leu Design 1.2
                                       (SEQ ID NO: 4)
GUCAGGAUGGCCGAGUGGUCUAAGGCGCCAGAUCAGUUAGUU

CUGGUCUCCGGAUGGAGCGUGGGUUCGAAUCCCACUUCUGAC

ACCA
```

-continued
tR-L9 = tRNA Leu Design 1.4
(SEQ ID NO: 6)
GUCAGGAUGGCCGAGUGGUCUAAGGCGCCAGACU<u>CAGUUA</u>UUC

UGGUCUCCGGAUGGAGCGUGGGUUCGAAUCCCACUUCUGACAC

CA

TABLE 3 tRNA variants tested for suppression.
Bold and underlined: anticodon tandem.
Numbering according to tRNA numbering convention.

| tRNA$^{Leu}$ variant | SEQ ID NO: | Anti-codon loop nt | Anticodon loop sequence 32-33-34-35-36-37-38 | SEQ ID NO: | Anti-codon tandem |
|---|---|---|---|---|---|
| tR-L1 | 46 | 10 nt | C-U-C-A-G-U-U-A-G-A | 51 | CAGUUA |
| tR-L2 | 47 | 10 nt | C-U-C-A-G-U-U-A-A-A | 52 | CAGUUA |
| tR-L3 | 3 | 10 nt | A-C-U-C-A-G-U-U-A-G | 53 | CAGUUA |
| tR-L4 | 48 | 9 nt | C-U-C-A-G-U-U-A-G | | CAGUUA |
| tR-L5 | 49 | 9 nt | C-U-C-A-G-U-U-A-A | | CAGUUA |
| tR-L6 | 50 | 9 nt | C-U-C-A-G-U-U-A-U | | CAGUUA |
| tR-L8 | 4 | 9 nt | A-U-C-A-G-U-U-A-G | | CAGUUA |
| tR-L9 | 6 | 9 nt | A-C-U-C-A-G-U-U-A | | CAGUUA |

The sequences of the tRNA variants are given in SEQ IDs NO: 3, 4, 6, 46-50, the sequences of the 10 nt anticodon loops in Table 3 are presented in SEQ ID NO: 51-53.

All modified tRNA were tested for readthrough (see FIG. 5). The most promising tRNA was tRL9 (T9, lower row, right, SEQ ID NO: 6) which led to significant read through and detection of mCherry. Further, asymmetric positioning of the anticodon tandem with total size of the anticodon loop of 9 nt were the most effective.

The invention claimed is:

1. A synthetic transfer RNA comprising an extended anticodon loop with two consecutive anticodon base triplets configured to base-pair to two consecutive codon base triplets on an mRNA,
wherein one of the two consecutive anticodon base triplets is configured to base-pair to a stop codon base triplet on the mRNA and the other of the two consecutive anticodon base triplets is configured to base-pair to a codon base triplet for leucine or a codon base triplet for alanine adjacent to the stop codon base triplet on the mRNA, and
wherein the synthetic transfer RNA is a suppressor tRNA that alters the reading of the mRNA in a translation system.

2. The synthetic transfer RNA according to claim 1, wherein the anticodon loop comprises 8 to 12 nucleotides.

3. The synthetic transfer RNA according to claim 2, wherein the anticodon loop comprises 9 nucleotides.

4. The synthetic transfer RNA according to claim 2, wherein the anticodon loop comprises 10 nucleotides.

5. The synthetic transfer RNA according to claim 1, wherein the two consecutive anticodon base triplets are asymmetrically arranged in the extended anticodon loop of the transfer RNA in relation to an imaginary symmetry axis longitudinally traversing through the stem of the anticodon arm and extended in the direction of the anticodon loop.

6. The synthetic transfer RNA according to claim 5, wherein the two consecutive anticodon base triplets are offset to the 3'-end of the synthetic transfer RNA.

7. The synthetic transfer RNA according to claim 1, wherein the transfer RNA is aminoacylated.

8. The synthetic transfer RNA according to claim 7, wherein the transfer RNA is aminoacylated with a dipeptide.

9. The synthetic transfer RNA according to claim 1, the synthetic transfer RNA comprising a T arm comprising, in 5'-3' direction in relation to the transfer RNA, a first T-stem sequence, a T-loop, and a second T-stem sequence, the second T-stem sequence being complementary to the first T-stem sequence, wherein the first T-stem sequence has the nucleotide sequence AGGGG and the second T-stem sequence has the nucleotide sequence CCCCU.

10. The synthetic transfer RNA according to claim 1, exhibiting a structure comprising an acceptor stem, a D arm, a T arm and an anticodon arm, wherein the D arm has a sequence of SEQ ID NO: 31.

11. The synthetic transfer RNA according to claim 1, the transfer RNA comprising an anticodon loop having a) a sequence selected from SEQ ID NO: 51, SEQ ID NO: 52, SEQ ID NO: 53, CUCAGUUAG, CUCAGUUAA, CUCAGUUAU, AUCAGUUAG, and ACUCAGUUA, or b) a sequence of a) above, wherein at least one of the nucleotides is replaced with a corresponding modified nucleotide.

12. The synthetic transfer RNA according to claim 1, wherein the nucleotides of the anticodon stem flanking the anticodon loop form a G-C or C-G pair.

13. A method for treating a disease which is at least partly caused by a nonsense mutation leading to premature cessation of translation of an mRNA, the method comprising administering a synthetic transfer RNA according to claim 1 to a patient with the disease.

14. A medicament for treating a disease, the medicament comprising a synthetic transfer RNA according to claim 1, wherein the disease is cystic fibrosis, Duchenne muscular dystrophy, neurofibromatosis type 1 or Hurler syndrome.

15. The medicament according to claim 14, wherein the disease is cystic fibrosis and the two consecutive anticodon base triplets of the extended anticodon loop have the sequence CAGUUA.

16. The medicament according to claim 15, wherein the transfer RNA comprises a) an anticodon loop having a sequence selected from SEQ ID NO: 51, SEQ ID NO: 52, SEQ ID NO: 53, CUCAGUUAG, CUCAGUUAA, CUCAGUUAU, AUCAGUUAG, and ACUCAGUUA, or b) an anticodon loop having one of the sequences in a) above, wherein at least one of the nucleotides is replaced with a corresponding modified nucleotide.

17. The medicament according to claim 16, wherein the extended anticodon loop comprises 9 nucleotides.

18. The synthetic transfer RNA of claim 1, wherein the two consecutive anticodon base triplets comprise the sequence of CAGUUA or UGCUCA.

19. The medicament of claim 14, wherein the two consecutive anticodon base triplets comprise the sequence of CAGUUA or UGCUCA.

* * * * *

SEQUENCE LISTING

```
Sequence total quantity: 57
SEQ ID NO: 1              moltype = RNA  length = 86
FEATURE                   Location/Qualifiers
modified_base             35
                          mod_base = m22g
source                    1..86
                          mol_type = other RNA
                          organism = Homo sapiens
SEQUENCE: 1
gtcaggatgg ccgagtggtc taaggcgcca gactnaagtt ctggtctccg gatggagcgt   60
gggttcgaat cccacttctg acacca                                        86

SEQ ID NO: 2              moltype = RNA  length = 86
FEATURE                   Location/Qualifiers
misc_feature              1..86
                          note = tRNA Leu with modified anticodon
source                    1..86
                          mol_type = other RNA
                          organism = synthetic construct
SEQUENCE: 2
gtcaggatgg ccgagtggtc taaggcgcca gacttaagtt ctggtctccg gatggagcgt   60
gggttcgaat cccacttctg acacca                                        86

SEQ ID NO: 3              moltype = RNA  length = 89
FEATURE                   Location/Qualifiers
misc_feature              1..89
                          note = tRNA design 1.1 with 10nt anticodon loop = tRNA-L3
misc_structure            32..41
                          note = /note="extended anticodon loop"
misc_feature              35..40
                          note = /note="anticodon tandem"
source                    1..89
                          mol_type = other RNA
                          organism = synthetic construct
SEQUENCE: 3
gtcaggatgg ccgagtggtc taaggcgcca gactcagtta gttctggtct ccggatggag   60
cgtgggttcg aatcccactt ctgacacca                                     89

SEQ ID NO: 4              moltype = RNA  length = 88
FEATURE                   Location/Qualifiers
misc_feature              1..88
                          note = tRNA design 1.2 with 9nt anticodon loop = tRNA-L8
misc_structure            32..40
                          note = /note="extended anticodon loop"
misc_feature              34..39
                          note = /note="anticodon tandem"
```

```
source                  1..88
                        mol_type = other RNA
                        organism = synthetic construct
SEQUENCE: 4
gtcaggatgg ccgagtggtc taaggcgcca gatcagttag ttctggtctc cggatggagc    60
gtgggttcga atcccacttc tgacacca                                       88

SEQ ID NO: 5            moltype = RNA  length = 88
FEATURE                 Location/Qualifiers
misc_feature            1..88
                        note = tRNA design 1.3 with 9nt anticodon loop
source                  1..88
                        mol_type = other RNA
                        organism = synthetic construct
SEQUENCE: 5
gtcaggatgg ccgagtggtc taaggcgcca gaccagttag ttctggtctc cggatggagc    60
gtgggttcga atcccacttc tgacacca                                       88

SEQ ID NO: 6            moltype = RNA  length = 88
FEATURE                 Location/Qualifiers
misc_feature            1..88
                        note = tRNA design 1.4 with 9nt anticodon loop = tRNA L9
misc_structure          32..40
                        note = /note="extended anticodon loop"
misc_feature            35..40
                        note = /note="anticodon tandem"
source                  1..88
                        mol_type = other RNA
                        organism = synthetic construct
SEQUENCE: 6
gtcaggatgg ccgagtggtc taaggcgcca gactcagtta ttctggtctc cggatggagc    60
gtgggttcga atcccacttc tgacacca                                       88

SEQ ID NO: 7            moltype = RNA  length = 88
FEATURE                 Location/Qualifiers
misc_feature            1..88
                        note = tRNA design 1.5 with 9nt anticodon loop
source                  1..88
                        mol_type = other RNA
                        organism = synthetic construct
SEQUENCE: 7
gtcaggatgg ccgagtggtc taaggcgcca gactcagtta gtctggtctc cggatggagc    60
gtgggttcga atcccacttc tgacacca                                       88

SEQ ID NO: 8            moltype = RNA  length = 83
FEATURE                 Location/Qualifiers
misc_feature            1..83
                        note = tRNA Leu CAG
source                  1..83
                        mol_type = tRNA
                        organism = Thermus thermophilus
SEQUENCE: 8
gccggggtgg cggaatgggt agacgcgcat gactcaggat catgtgcgca agcgtgcggg    60
ttcaagtccc gccccggca cca                                             83

SEQ ID NO: 9            moltype = RNA  length = 88
FEATURE                 Location/Qualifiers
misc_feature            1..88
                        note = tRNA design 2.1
misc_feature            35..40
                        note = /note="anticodon tandem"
source                  1..88
                        mol_type = other RNA
                        organism = synthetic construct
SEQUENCE: 9
ggcaggctga gggagatggt caacctagcc agctcagtta gctggctctc cggatggagc    60
gtggcttcga atgccacgcc tgccacca                                       88

SEQ ID NO: 10           moltype = RNA  length = 88
FEATURE                 Location/Qualifiers
misc_feature            1..88
                        note = tRNA design 2.2
misc_feature            35..40
                        note = /note="anticodon tandem"
source                  1..88
                        mol_type = other RNA
                        organism = synthetic construct
SEQUENCE: 10
gacaggctga gggagatggt caacctagca gcctcagtta ggctgctctc cggatggagc    60
```

```
gtggcttcga atgccacgcc tgtcacca                                         88

SEQ ID NO: 11            moltype = RNA   length = 88
FEATURE                  Location/Qualifiers
misc_feature             1..88
                         note = tRNA design 2.3
misc_feature             35..40
                         note = /note="anticodon tandem"
source                   1..88
                         mol_type = other RNA
                         organism = synthetic construct
SEQUENCE: 11
gccagcctga gggagatggt caacctagcc agctcagtta gctggctctc cggatggagc     60
gtggcttcga atgccacggc tggcacca                                         88

SEQ ID NO: 12            moltype = RNA   length = 88
FEATURE                  Location/Qualifiers
misc_feature             1..88
                         note = tRNA design 2.4
misc_feature             35..40
                         note = /note="anticodon tandem"
source                   1..88
                         mol_type = other RNA
                         organism = synthetic construct
SEQUENCE: 12
ggcagcctga gggagatggt caacctagca gcctcagtta ggctgctctc cggatggagc     60
gtggcttcga atgccacggc tgccacca                                         88

SEQ ID NO: 13            moltype = RNA   length = 88
FEATURE                  Location/Qualifiers
misc_feature             1..88
                         note = tRNA design 2.5
misc_feature             35..40
                         note = /note="anticodon tandem"
source                   1..88
                         mol_type = other RNA
                         organism = synthetic construct
SEQUENCE: 13
gccagcctga gggagatggt caacctaggt gcctcagtta ggcacctctc cggatggagc     60
gtggcttcga atgccacggc tggcacca                                         88

SEQ ID NO: 14            moltype = RNA   length = 88
FEATURE                  Location/Qualifiers
misc_feature             1..88
                         note = tRNA design 2.6
misc_feature             35..40
                         note = /note="anticodon tandem"
source                   1..88
                         mol_type = other RNA
                         organism = synthetic construct
SEQUENCE: 14
gccagcctga gggagatggt caacctactg gactcagtta gtccagtctc cggatggagc     60
gtggcttcga atgccacggc tggcacca                                         88

SEQ ID NO: 15            moltype = RNA   length = 88
FEATURE                  Location/Qualifiers
misc_feature             1..88
                         note = tRNA design 2.7
misc_feature             35..40
                         note = /note="anticodon tandem"
source                   1..88
                         mol_type = other RNA
                         organism = synthetic construct
SEQUENCE: 15
gccagcctga gggagatggt caacctaccg gactcagtta gtccggtctc cggatggagc     60
gtggcttcga atgccacggc tggcacca                                         88

SEQ ID NO: 16            moltype = RNA   length = 88
FEATURE                  Location/Qualifiers
misc_feature             1..88
                         note = tRNA design 2.8
misc_feature             35..40
                         note = /note="anticodon tandem"
source                   1..88
                         mol_type = other RNA
                         organism = synthetic construct
SEQUENCE: 16
gccagcctga gggagatggt caacctacct gcctcagtta ggcaggtctc cggatggagc     60
gtggcttcga atgccacggc tggcacca                                         88
```

```
SEQ ID NO: 17            moltype = RNA   length = 88
FEATURE                  Location/Qualifiers
misc_feature             1..88
                         note = tRNA design 2.9
misc_feature             35..40
                         note = /note="anticodon tandem"
source                   1..88
                         mol_type = other RNA
                         organism = synthetic construct
SEQUENCE: 17
gccaggctga gggagatggt caacctagct cactcagtta gtgagctctc cggatggagc   60
gtggcttcga atgccacgcc tggcacca                                     88

SEQ ID NO: 18            moltype = RNA   length = 72
FEATURE                  Location/Qualifiers
misc_feature             1..72
                         note = tRNA Ala-AGC
source                   1..72
                         mol_type = tRNA
                         organism = Homo sapiens
SEQUENCE: 18
ggggaattag ctcaaatggt agagcgctcg cttagcatgc gagaggtagc gggatcgatg   60
cccgcattct cc                                                      72

SEQ ID NO: 19            moltype = RNA   length = 79
FEATURE                  Location/Qualifiers
misc_feature             1..79
                         note = tRNA design 3.1
misc_feature             34..39
                         note = /note="anticodon tandem"
source                   1..79
                         mol_type = other RNA
                         organism = synthetic construct
SEQUENCE: 19
ggggaattag ctcaaatggt agagcgctcg ctttgctcaa tgcgagaggt agcgggatcg   60
atgcccgcat tctccacca                                               79

SEQ ID NO: 20            moltype = RNA   length = 78
FEATURE                  Location/Qualifiers
misc_feature             1..78
                         note = tRNA design 3.2
misc_feature             33..38
                         note = /note="anticodon tandem"
source                   1..78
                         mol_type = other RNA
                         organism = synthetic construct
SEQUENCE: 20
ggggaattag ctcaaatggt agagcgctcg cttgctcaat gcgagaggta gcgggatcga   60
tgcccgcatt ctccacca                                                78

SEQ ID NO: 21            moltype = RNA   length = 78
FEATURE                  Location/Qualifiers
misc_feature             1..78
                         note = tRNA design 3.3
misc_feature             34..39
                         note = /note="anticodon tandem"
source                   1..78
                         mol_type = other RNA
                         organism = synthetic construct
SEQUENCE: 21
ggggaattag ctcaaatggt agagcgctcg ctttgctcat gcgagaggta gcgggatcga   60
tgcccgcatt ctccacca                                                78

SEQ ID NO: 22            moltype = RNA   length = 78
FEATURE                  Location/Qualifiers
misc_feature             1..78
                         note = tRNA design 3.4
misc_feature             34..39
                         note = /note="anticodon tandem"
source                   1..78
                         mol_type = other RNA
                         organism = synthetic construct
SEQUENCE: 22
ggggaattag ctcaaatggt agagcgctcg ctttgctcaa gcgagaggta gcgggatcga   60
tgcccgcatt ctccacca                                                78

SEQ ID NO: 23            moltype = RNA   length = 78
FEATURE                  Location/Qualifiers
```

| | | |
|---|---|---|
| misc_feature | 1..78 | |
| | note = 2x3nt anticodon tRNA based on Ala tRNA | |
| misc_difference | 5..7 | |
| | note = n = A, C, G or U, or any modified base | |
| misc_difference | 16..17 | |
| | note = n = A, C, G or U, or any modified base | |
| misc_difference | 27..31 | |
| | note = n = A, C, G or U, or any modified base | |
| misc_feature | 34..39 | |
| | note = /note="anticodon tandem" | |
| misc_difference | 41..45 | |
| | note = n = A, C, G or U, or any modified base | |
| misc_difference | 47 | |
| | note = n = A, C, G or U, or any modified base | |
| misc_difference | 49 | |
| | note = n = A, C, G or U, or any modified base | |
| misc_difference | 51..54 | |
| | note = n = A, C, G or U, or any modified base | |
| misc_difference | 64..70 | |
| | note = n = A, C, G or U, or any modified base | |
| source | 1..78 | |
| | mol_type = other RNA | |
| | organism = synthetic construct | |

SEQUENCE: 23

```
ggggnnntag ctcagnnggt agagcgnnnn ncttgctcaa nnnnnangnc nnnngttcga    60
tccnnnnnnn ctccacca                                                 78
```

| | | |
|---|---|---|
| SEQ ID NO: 24 | moltype = RNA   length = 74 | |
| FEATURE | Location/Qualifiers | |
| misc_feature | 1..74 | |
| | note = 2x3nt anticodon tRNA based on Ala tRNA without CCA tail | |
| misc_difference | 5..7 | |
| | note = n = A, C, G or U, or any modified base | |
| misc_difference | 16..17 | |
| | note = n = A, C, G or U, or any modified base | |
| misc_difference | 27..31 | |
| | note = n = A, C, G or U, or any modified base | |
| misc_feature | 34..39 | |
| | note = /note="anticodon tandem" | |
| misc_difference | 41..45 | |
| | note = n = A, C, G or U, or any modified base | |
| misc_difference | 47 | |
| | note = n = A, C, G or U, or any modified base | |
| misc_difference | 49 | |
| | note = n = A, C, G or U, or any modified base | |
| misc_difference | 51..54 | |
| | note = n = A, C, G or U, or any modified base | |
| misc_difference | 64..70 | |
| | note = n = A, C, G or U, or any modified base | |
| source | 1..74 | |
| | mol_type = other RNA | |
| | organism = synthetic construct | |

SEQUENCE: 24

```
ggggnnntag ctcagnnggt agagcgnnnn ncttgctcaa nnnnnangnc nnnngttcga    60
tccnnnnnnn ctcc                                                     74
```

| | | |
|---|---|---|
| SEQ ID NO: 25 | moltype = RNA   length = 78 | |
| FEATURE | Location/Qualifiers | |
| misc_feature | 1..78 | |
| | note = tRNA with extended anticodon loop | |
| misc_difference | 32..40 | |
| | note = n = A, C, G or U, or any modified base | |
| misc_structure | 32..40 | |
| | note = /note="extended anticodon loop" | |
| source | 1..78 | |
| | mol_type = other RNA | |
| | organism = synthetic construct | |

SEQUENCE: 25

```
ggggcggtag ctcagaaggg agagcagcgg annnnnnnnn tccgcgagac ggtccttcga    60
ttggaccccg ctccacca                                                 78
```

| | | |
|---|---|---|
| SEQ ID NO: 26 | moltype = RNA   length = 76 | |
| FEATURE | Location/Qualifiers | |
| misc_feature | 1..76 | |
| | note = tRNA with extended anticodon loop | |
| misc_feature | 31..39 | |
| | note = /note="extended anticodon loop" | |
| misc_difference | 31..39 | |

```
                        note = n = A, C, G or U, or any modified base
source                  1..76
                        mol_type = other RNA
                        organism = synthetic construct
SEQUENCE: 26
ggggcggtag ctcagaaggg agagcagcgg nnnnnnnnnc cgcgagacag gggttcgatt    60
cccctccgct ccacca                                                   76

SEQ ID NO: 27           moltype = RNA  length = 77
FEATURE                 Location/Qualifiers
misc_feature            1..77
                        note = tRNA with extended anticodon loop
misc_feature            10..26
                        note = /note="D arm"
misc_difference         32..40
                        note = n = A, C, G or U, or any modified base
misc_structure          32..40
                        note = /note="extended anticodon loop"
source                  1..77
                        mol_type = other RNA
                        organism = synthetic construct
SEQUENCE: 27
ggggcggtag cgcagcctgg tagcgcagcg gnnnnnnnnn ccgcgagaca ggggttcgat    60
tcccctccgc tccacca                                                  77

SEQ ID NO: 28           moltype = RNA  length = 78
FEATURE                 Location/Qualifiers
misc_feature            1..78
                        note = tRNA with extended anticodon loop
misc_structure          32..40
                        note = /note="extended anticodon loop"
source                  1..78
                        mol_type = other RNA
                        organism = synthetic construct
SEQUENCE: 28
ggggcggtag ctcagaaggg agagcagcgg acttgctcaa tccgcgagac ggtccttcga    60
ttggaccccg ctccacca                                                 78

SEQ ID NO: 29           moltype = RNA  length = 76
FEATURE                 Location/Qualifiers
misc_feature            1..76
                        note = tRNA with extended anticodon loop
misc_structure          31..39
                        note = /note="extended anticodon loop"
source                  1..76
                        mol_type = other RNA
                        organism = synthetic construct
SEQUENCE: 29
ggggcggtag ctcagaaggg agagcagcgg cttgctcaac cgcgagacag gggttcgatt    60
cccctccgct ccacca                                                   76

SEQ ID NO: 30           moltype = RNA  length = 77
FEATURE                 Location/Qualifiers
misc_feature            1..77
                        note = tRNA with extended anticodon loop
misc_feature            10..26
                        note = /note="D arm"
misc_structure          32..40
                        note = /note="extended anticodon loop"
source                  1..77
                        mol_type = other RNA
                        organism = synthetic construct
SEQUENCE: 30
ggggcggtag cgcagcctgg tagcgcagcg gcttgctcaa ccgcgagaca ggggttcgat    60
tcccctccgc tccacca                                                  77

SEQ ID NO: 31           moltype = RNA  length = 17
FEATURE                 Location/Qualifiers
misc_feature            1..17
                        note = modified D-arm
source                  1..17
                        mol_type = other RNA
                        organism = synthetic construct
SEQUENCE: 31
gcgcagcctg gtagcgc                                                  17

SEQ ID NO: 32           moltype = DNA  length = 17
FEATURE                 Location/Qualifiers
misc_feature            1..17
```

```
                        note         = T7 promoter
source                  1..17
                        mol_type     = other DNA
                        organism     = T7-like viruses
SEQUENCE: 32
taatacgact cactata                                                  17

SEQ ID NO: 33           moltype = RNA   length = 76
FEATURE                 Location/Qualifiers
misc_feature            1..76
                        note         = n1 tRNA with antistop codon
misc_structure          34..36
                        note         = /note="antistop codon"
source                  1..76
                        mol_type     = other RNA
                        organism     = synthetic construct
SEQUENCE: 33
ggggcggtag ctcagaaggg agagcagcgg agatcaaatc cgcgagacgg tccttcgatt   60
ggacccgct ccacca                                                    76

SEQ ID NO: 34           moltype = RNA   length = 76
FEATURE                 Location/Qualifiers
misc_feature            1..76
                        note         = n2 tRNA with antistop codon
misc_structure          34..36
                        note         = /note="antistop codon"
source                  1..76
                        mol_type     = other RNA
                        organism     = synthetic construct
SEQUENCE: 34
ggggctctag ctcagaaggg agagcaggga cgatcaaagt cccgagacgg cgcttcgatt   60
gcgccgagct ccacca                                                   76

SEQ ID NO: 35           moltype = RNA   length = 76
FEATURE                 Location/Qualifiers
misc_feature            1..76
                        note         = n3 tRNA with antistop codon
misc_structure          34..36
                        note         = /note="antistop codon"
source                  1..76
                        mol_type     = other RNA
                        organism     = synthetic construct
SEQUENCE: 35
ggggccctag ctcagaaagg agagcaggca ggatcaaact gccgagaagc agcgacataa   60
gctgcgggct ccacca                                                   76

SEQ ID NO: 36           moltype = RNA   length = 76
FEATURE                 Location/Qualifiers
misc_feature            1..76
                        note         = n4 tRNA with antistop codon
misc_structure          34..36
                        note         = /note="antistop codon"
source                  1..76
                        mol_type     = other RNA
                        organism     = synthetic construct
SEQUENCE: 36
ggggccctag ctcagaaagg agagcaggca ggactaaact gccgagaagc cgggactaaa   60
ccggcgggct ccacca                                                   76

SEQ ID NO: 37           moltype = RNA   length = 76
FEATURE                 Location/Qualifiers
misc_feature            1..76
                        note         = n5 tRNA with antistop codon
misc_structure          34..36
                        note         = /note="antistop codon"
source                  1..76
                        mol_type     = other RNA
                        organism     = synthetic construct
SEQUENCE: 37
ggggcgctag ctcaataagg agagcaggag cgactaaagc tccgagaagt cgcgacataa   60
gcgacgcgct ccacca                                                   76

SEQ ID NO: 38           moltype = RNA   length = 76
FEATURE                 Location/Qualifiers
misc_feature            1..76
                        note         = n6 tRNA with antistop codon
misc_structure          34..36
                        note         = /note="antistop codon"
source                  1..76
```

```
                        mol_type = other RNA
                        organism = synthetic construct
SEQUENCE: 38
ggggcggaac agggaaacag acctgagcgg agactaaatc cgcaataagg tccgaactaa    60
ggaccccgct ccacca                                                    76

SEQ ID NO: 39           moltype = RNA   length = 76
FEATURE                 Location/Qualifiers
misc_feature            1..76
                        note = Human Ala tRNA (GGC)
misc_structure          34..36
                        note = /note="anticodon"
source                  1..76
                        mol_type = tRNA
                        organism = Homo sapiens
SEQUENCE: 39
ggggctatag ctcagctggg agagcgcttg catggcatgc aagaggtcag cggttcgatc    60
ccgcttagct ccacca                                                    76

SEQ ID NO: 40           moltype = RNA   length = 76
FEATURE                 Location/Qualifiers
misc_feature            1..76
                        note = Human Ala tRNA (UGC)
misc_structure          34..36
                        note = /note="anticodon"
source                  1..76
                        mol_type = tRNA
                        organism = Homo sapiens
SEQUENCE: 40
ggggctatag ctcagctggg agagcgcctg ctttgcacgc aggaggtctg cggttcgatc    60
ccgcatagct ccacca                                                    76

SEQ ID NO: 41           moltype = RNA   length = 76
FEATURE                 Location/Qualifiers
misc_feature            1..76
                        note = Human tRNA Ala with antistop codon
misc_structure          34..36
                        note = /note="antistop codon"
source                  1..76
                        mol_type = other RNA
                        organism = synthetic construct
SEQUENCE: 41
ggggctatag ctcagctggg agagcgcctg ctttcaacgc aggaggtctg cggttcgatc    60
ccgcatagct ccacca                                                    76

SEQ ID NO: 42           moltype = RNA   length = 76
FEATURE                 Location/Qualifiers
misc_feature            1..76
                        note = TS1: tRNA with antistop codon and modified T-stem
misc_structure          34..36
                        note = /note="antistop codon"
misc_structure          49..53
                        note = /note="T-stem"
misc_structure          61..65
                        note = /note="T-stem"
source                  1..76
                        mol_type = other RNA
                        organism = synthetic construct
SEQUENCE: 42
ggggcggtag ctcagaaggg agagcagcgg ccttcagagc cgcgagactg cccttcgatt    60
gggcaccgct ccacca                                                    76

SEQ ID NO: 43           moltype = RNA   length = 76
FEATURE                 Location/Qualifiers
misc_feature            1..76
                        note = TS2: tRNA with antistop codon and modified T-stem
misc_structure          34..36
                        note = /note="antistop codon"
misc_structure          49..53
                        note = /note="T-stem"
misc_structure          61..65
                        note = /note="T-stem"
source                  1..76
                        mol_type = other RNA
                        organism = synthetic construct
SEQUENCE: 43
ggggcggtag ctcagaaggg agagcagcgg ccttcagagc cgcgagacag gggttcgatt    60
cccctccgct ccacca                                                    76
```

| | | |
|---|---|---|
| SEQ ID NO: 44 | moltype = RNA  length = 77 | |
| FEATURE | Location/Qualifiers | |
| misc_feature | 1..77 | |
| | note = DTS1: tRNA with antistop codon, modified T-stem and modifiedD-Loop | |
| misc_structure | 10..26 | |
| | note = /note="D arm" | |
| misc_structure | 35..37 | |
| | note = /note="antistop codon" | |
| misc_structure | 50..54 | |
| | note = /note="T-stem" | |
| misc_structure | 62..66 | |
| | note = /note="T-stem" | |
| source | 1..77 | |
| | mol_type = other RNA | |
| | organism = synthetic construct | |
| SEQUENCE: 44 | | |
| ggggcggtag cgcagcctgg tagcgcagcg gccttcagag ccgcgagact gcccttcgat | | 60 |
| tgggcaccgc tccacca | | 77 |

| | | |
|---|---|---|
| SEQ ID NO: 45 | moltype = RNA  length = 77 | |
| FEATURE | Location/Qualifiers | |
| misc_feature | 1..77 | |
| | note = DTS2: tRNA with antistop codon, modified T-stem and modifiedD-Loop | |
| misc_binding | 10..26 | |
| | bound_moiety = 10...26 | |
| | note = /note="D arm" | |
| misc_structure | 35..37 | |
| | note = /note="antistop codon" | |
| misc_structure | 50..54 | |
| | note = /note="T-stem" | |
| misc_structure | 62..66 | |
| | note = /note="T-stem" | |
| source | 1..77 | |
| | mol_type = other RNA | |
| | organism = synthetic construct | |
| SEQUENCE: 45 | | |
| ggggcggtag cgcagcctgg tagcgcagcg gccttcagag ccgcgagaca ggggttcgat | | 60 |
| tccccteege tccacca | | 77 |

| | | |
|---|---|---|
| SEQ ID NO: 46 | moltype = RNA  length = 89 | |
| FEATURE | Location/Qualifiers | |
| misc_feature | 1..89 | |
| | note = tRNA-L1 with extended anticodon loop | |
| misc_structure | 32..41 | |
| | note = /note="extended anticodon loop" | |
| misc_feature | 34..39 | |
| | note = /note="anticodon tandem" | |
| source | 1..89 | |
| | mol_type = other RNA | |
| | organism = synthetic construct | |
| SEQUENCE: 46 | | |
| gtcaggatgg ccgagtggtc taaggcgcca cctcagttag agtctggtct ccggatggag | | 60 |
| cgtgggttcg aatcccactt ctgacacca | | 89 |

| | | |
|---|---|---|
| SEQ ID NO: 47 | moltype = RNA  length = 89 | |
| FEATURE | Location/Qualifiers | |
| misc_feature | 1..89 | |
| | note = tRNA-L2 with extended anticodon loop | |
| misc_structure | 32..41 | |
| | note = /note="extended anticodon loop" | |
| misc_feature | 34..39 | |
| | note = /note="anticodon tandem" | |
| source | 1..89 | |
| | mol_type = other RNA | |
| | organism = synthetic construct | |
| SEQUENCE: 47 | | |
| gtcaggatgg ccgagtggtc taaggcgcca cctcagttaa agtctggtct ccggatggag | | 60 |
| cgtgggttcg aatcccactt ctgacacca | | 89 |

| | | |
|---|---|---|
| SEQ ID NO: 48 | moltype = RNA  length = 88 | |
| FEATURE | Location/Qualifiers | |
| misc_feature | 1..88 | |
| | note = tRNA-L4 with extended anticodon loop | |
| misc_structure | 32..40 | |
| | note = /note="extended anticodon loop" | |
| misc_feature | 34..39 | |
| | note = /note="anticodon tandem" | |

```
source                    1..88
                          mol_type = other RNA
                          organism = synthetic construct
SEQUENCE: 48
gtcaggatgg ccgagtggtc taaggcgcca cctcagttag gtctggtctc cggatggagc    60
gtgggttcga atcccacttc tgacacca                                       88

SEQ ID NO: 49             moltype = RNA   length = 88
FEATURE                   Location/Qualifiers
misc_feature              1..88
                          note = tRNA-L5 with extended anticodon loop
misc_structure            32..40
                          note = /note="extended anticodon loop"
misc_feature              34..39
                          note = /note="anticodon tandem"
source                    1..88
                          mol_type = other RNA
                          organism = synthetic construct
SEQUENCE: 49
gtcaggatgg ccgagtggtc taaggcgcca cctcagttaa gtctggtctc cggatggagc    60
gtgggttcga atcccacttc tgacacca                                       88

SEQ ID NO: 50             moltype = RNA   length = 88
FEATURE                   Location/Qualifiers
misc_feature              1..88
                          note = tRNA-L6 with extended anticodon loop
misc_structure            32..40
                          note = /note="extended anticodon loop"
misc_feature              34..39
                          note = /note="anticodon tandem"
source                    1..88
                          mol_type = other RNA
                          organism = synthetic construct
SEQUENCE: 50
gtcaggatgg ccgagtggtc taaggcgcca cctcagttat gtctggtctc cggatggagc    60
gtgggttcga atcccacttc tgacacca                                       88

SEQ ID NO: 51             moltype = RNA   length = 10
FEATURE                   Location/Qualifiers
misc_feature              1..10
                          note = tR-L1 anticodon loop
source                    1..10
                          mol_type = other RNA
                          organism = synthetic construct
SEQUENCE: 51
ctcagttaga                                                           10

SEQ ID NO: 52             moltype = RNA   length = 10
FEATURE                   Location/Qualifiers
misc_feature              1..10
                          note = tR-L2 anticodon loop
source                    1..10
                          mol_type = other RNA
                          organism = synthetic construct
SEQUENCE: 52
ctcagttaaa                                                           10

SEQ ID NO: 53             moltype = RNA   length = 10
FEATURE                   Location/Qualifiers
misc_feature              1..10
                          note = tR-L3 anticodon loop
source                    1..10
                          mol_type = other RNA
                          organism = synthetic construct
SEQUENCE: 53
actcagttag                                                           10

SEQ ID NO: 54             moltype = RNA   length = 20
FEATURE                   Location/Qualifiers
misc_feature              1..20
                          note = V loop tRNA selenocysteine
source                    1..20
                          mol_type = other RNA
                          organism = synthetic construct
SEQUENCE: 54
ttggggccgc gcggtcccgg                                                20

SEQ ID NO: 55             moltype = RNA   length = 79
FEATURE                   Location/Qualifiers
```

```
misc_feature        1..79
                    note = tRNA with extended anticodon loop
misc_difference     32..41
                    note = n = A, C, G or U, or any modified base
misc_structure      32..41
                    note = /note="extended anticodon loop"
source              1..79
                    mol_type = other RNA
                    organism = synthetic construct
SEQUENCE: 55
ggggcggtag ctcagaaggg agagcagcgg annnnnnnnn ntccgcgaga cggtccttcg   60
attggacccc gctccacca                                                79

SEQ ID NO: 56       moltype = RNA  length = 77
FEATURE             Location/Qualifiers
misc_feature        1..77
                    note = tRNA with extended anticodon loop
misc_difference     31..40
                    note = n = A, C, G or U, or any modified base
misc_structure      31..40
                    note = /note="extended anticodon loop"
misc_feature        50..54
                    note = /note="T stem"
misc_feature        62..66
                    note = /note="T stem"
source              1..77
                    mol_type = other RNA
                    organism = synthetic construct
SEQUENCE: 56
ggggcggtag ctcagaaggg agagcagcgg nnnnnnnnnn ccgcgagaca ggggttcgat   60
tccccctccgc tccacca                                                 77

SEQ ID NO: 57       moltype = RNA  length = 78
FEATURE             Location/Qualifiers
misc_feature        1..78
                    note = tRNA with extended anticodon loop
misc_feature        10..26
                    note = /note="D arm"
misc_difference     32..41
                    note = n = A, C, G or U, or any modified base
misc_structure      32..41
                    note = /note="extended anticodon loop"
misc_feature        51..55
                    note = /note="T stem"
misc_feature        63..67
                    note = /note="T stem"
source              1..78
                    mol_type = other RNA
                    organism = synthetic construct
SEQUENCE: 57
ggggcggtag cgcagcctgg tagcgcagcg gnnnnnnnnn nccgcgagac aggggttcga   60
ttcccctccg ctccacca                                                 78
```